(12) United States Patent
Bisso et al.

(10) Patent No.: US 10,533,133 B2
(45) Date of Patent: Jan. 14, 2020

(54) RARE EARTH SPATIAL/SPECTRAL MICROPARTICLE BARCODES FOR LABELING OF OBJECTS AND TISSUES

(71) Applicant: Massachusetts Institute of Technology, Cambridge, MA (US)

(72) Inventors: Paul Bisso, Belmont, MA (US); Albert Swiston, Baltimore, MD (US); Jiseok Lee, Melrose, MA (US); Patrick S. Doyle, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/387,889

(22) Filed: Dec. 22, 2016

(65) Prior Publication Data

US 2017/0226416 A1    Aug. 10, 2017

Related U.S. Application Data

(63) Continuation of application No. 14/214,528, filed on Mar. 14, 2014, now Pat. No. 9,528,144.
(Continued)

(51) Int. Cl.
*C09K 11/02* (2006.01)
*C09K 11/77* (2006.01)
(Continued)

(52) U.S. Cl.
CPC .......... *C09K 11/7773* (2013.01); *C09K 11/02* (2013.01); *C09K 11/025* (2013.01); *C12Q 1/6825* (2013.01); *G01N 21/6428* (2013.01); *G01N 21/6486* (2013.01); *G07D 7/0043* (2017.05); *G07D 7/1205* (2017.05); *G07D 7/2033* (2013.01); *G01N 2021/6439* (2013.01);
(Continued)

(58) Field of Classification Search
CPC ............ C09K 11/7773; C09K 11/7772; C09K 11/7766; C09K 11/77; C09K 11/08; G07D 7/1205; G07D 7/12; G07D 7/07
USPC .................................. 436/164, 169, 172, 56
See application file for complete search history.

(56) References Cited

U.S. PATENT DOCUMENTS

| | | |
|---|---|---|
| 5,674,698 A | 10/1997 | Zarling et al. |
| 5,698,397 A | 12/1997 | Zarling et al. |

(Continued)

FOREIGN PATENT DOCUMENTS

| | | |
|---|---|---|
| CA | 2125228 A1 | 12/1994 |
| EP | 2060916 A1 | 5/2009 |

(Continued)

OTHER PUBLICATIONS

Yoon et al, Recent functional material based approaches to prevent and detect counterfeiting, Journal of Materials Chemistry C, Jan. 2013, 1, 2388-2403. (Year: 2013).*

(Continued)

*Primary Examiner* — Christine T Mui
(74) *Attorney, Agent, or Firm* — McCarter & English, LLP; David R. Burns

(57) ABSTRACT

Polymer microparticles spatially and spectrally encoded using upconversion nanocrystals (UCN) are described for labeling of articles and tissues. UCN having spectrally distinguishable emission spectra are disposed in different portions of an encoding region of each microparticle.

21 Claims, 35 Drawing Sheets
(14 of 35 Drawing Sheet(s) Filed in Color)

Related U.S. Application Data

(60) Provisional application No. 61/800,995, filed on Mar. 15, 2013, provisional application No. 61/801,351, filed on Mar. 15, 2013.

(51) Int. Cl.
| | |
|---|---|
| *G01N 21/64* | (2006.01) |
| *C12Q 1/6825* | (2018.01) |
| *G07D 7/2033* | (2016.01) |
| *G07D 7/0043* | (2016.01) |
| *G07D 7/1205* | (2016.01) |
| *C09K 11/00* | (2006.01) |

(52) U.S. Cl.
CPC .... *Y10T 436/13* (2015.01); *Y10T 436/143333* (2015.01)

(56) References Cited

U.S. PATENT DOCUMENTS

| | | | |
|---|---|---|---|
| 7,874,489 B2 | 1/2011 | Mercolino | |
| 7,947,487 B2 | 5/2011 | Doyle et al. | |
| 8,220,716 B2 | 7/2012 | Mercolino | |
| 8,247,018 B2 | 8/2012 | Mercolino | |
| 8,458,475 B2 | 6/2013 | Mercolino | |
| 9,053,364 B2 | 6/2015 | Mercolino et al. | |
| 2005/0272049 A1* | 12/2005 | Banerjee | B01J 19/0046 435/6.11 |
| 2006/0269483 A1 | 11/2006 | Austin et al. | |
| 2010/0041017 A1 | 2/2010 | Tsukada et al. | |
| 2010/0172898 A1 | 7/2010 | Doyle et al. | |
| 2010/0261263 A1 | 10/2010 | Vo-Dinh et al. | |
| 2011/0127445 A1 | 6/2011 | Zhang et al. | |
| 2011/0189777 A1 | 8/2011 | Graziano et al. | |
| 2011/0263747 A1 | 10/2011 | Doyle et al. | |
| 2011/0306065 A1 | 12/2011 | Friedberg et al. | |
| 2012/0003755 A1 | 1/2012 | Chapin et al. | |
| 2012/0107820 A1 | 5/2012 | Pregibon et al. | |
| 2012/0273564 A1 | 11/2012 | Mercolino et al. | |
| 2012/0280144 A1 | 11/2012 | Guilfoyle et al. | |
| 2013/0193346 A1 | 8/2013 | Justel et al. | |
| 2013/0244894 A1 | 9/2013 | Mercolino | |
| 2013/0273559 A1 | 10/2013 | Tousch et al. | |
| 2014/0148880 A1 | 5/2014 | Deisseroth et al. | |
| 2014/0273246 A1 | 9/2014 | Bisso et al. | |
| 2015/0192518 A1 | 7/2015 | Baxter et al. | |

FOREIGN PATENT DOCUMENTS

| | | |
|---|---|---|
| WO | 2010107720 A2 | 9/2010 |
| WO | 2011156434 A2 | 12/2011 |

OTHER PUBLICATIONS

Appleyard, et al., "Bar-coded hydrogel microparticles for protein detection: synthesis, assay and scanning", Nature Protocols, Oct. 2, 2011, vol. 6, No. 11, pp. 1761-1774.
Battersby, et al., "Toward Larger Chemical Libraries: Encoding with Fluorescent Colloids in Combinatorial Chemistry", Journal American Chemical Society, Feb. 17, 2000, pp. 2138-2139.
Birtwell, et al., "Microparticle encoding technologies for high-throughput multiplexed suspension assays", The Royal Society of Chemistry, Integrative Biology, Jun. 2009, vol. 1, pp. 345-362.
Bogdan, et al., "Synthesis of Ligand-Free Colloidally Stable Water Dispersible Brightly Luminescent Lanthanide-Doped Upconverting Nanoparticles", Nano Letters (ACS), Jan. 18, 2011, vol. 11, pp. 835-840.
Bong, et al., "Hydrodynamic Focusing Lithography", Angewandte Chemie International Edition, Nov. 30, 2009, 49, pp. 87-90.
Bong, et al., "Non-polydimethylsiloxane devices for oxygen-free flow lithography", Nature Communications, May 1, 2012, 3:805, DOI: 10.1038/ncomms1800.
Braeckmans, et al., "Encoding microcarriers by spatial selective photobleaching," Nature Materials, Mar. 2003, vol. 2, pp. 169-173.
Cederquist, et al., "Encoded anisotropic particles for multiplexed bioanalysis", Wiley Interdisciplinary Reviews: Nanomedicin and Nanobiotechnology, Nov./Dec. 2010, vol. 2, pp. 578-600. First published online Jun. 8, 2010.
Chapin, et al., "Rapid microRNA Profiling on Encoded Gel Microparticles", Angewandte Chemie International Edition, Jan. 26, 2011, vol. 55, pp. 2289-2293.
Chapin, et al., "Ultrasensitive Multiplexed MicroRNA Quantification on Encoded Gel Microparticles Using Rolling Circle Amplification", Analytical Chemistry, Aug. 3, 2011, vol. 83, pp. 7179-7185.
Chen, et al., "Versatile Synthesis Strategy for Carboxylic Acid-functionalized Upconverting Nanophosphors as Biological Labels", Journal of the American Chemical Society, Feb. 16, 2008, vol. 130, pp. 3023-3029.
Choi, et al., "Multiplexed Detection of mRNA Using Porosity-Tuned Hydrogel Microparticles", Analytical Chemistry, Sep. 28, 2012, 84, pp. 9370-9378.
Cunin, et al., "Biomolecular screening with encoded porous-silicon photonic crystals", Nature Materials, vol. 1, pp. 39-41, Sep. 2002.
Dejneka, et al., "Rare earth-doped glass microbarcodes", Proceedings of the National Academy of Sciences, Jan. 21, 2003, vol. 100, No. 2, pp. 389-393.
Dendukuri, et al., "Continuous-flow lithography for high-throughput microparticle synthesis", Nature Materials, vol. 5, May 2006, pp. 365-369.
Dendukuri, et al., "Stop-flow lithography in a microfluidic device", Lab on a Chip, The Royal Society of Chemistry, May 21, 2007, vol. 7, pp. 818-828.
Examination Report for Australian Patent Application No. 2014228412 by IP Australia dated Feb. 24, 2017.
Fulton, et al., "Advanced multiplexed analysis with the FlowMetrix™ system", Clinical Chemistry 43:9; pp. 1749-1756, Sep. 1997.
Gerver, et al., "Programmable microfluidic synthesis of spectrally encoded microspheres", Lab on a Chip, The Royal Society of Chemistry, Sep. 25, 2012, 12, pp. 4716-4723.
Gorris et al., "Photon-upconverting nanoparticles for optical encoding and multiplexing of cells, biomolecules, and microspheres", Angewandte Chemie International Edition, 52 (13): pp. 3584-3600 (Feb. 28, 2013).
Gorris, et al., "Tuning the Dual Emission of Photon-Upconverting Nanoparticles for Ratiometric Multiplexed Encoding", Advanced Materials, Feb. 23, 2011, vol. 23, pp. 1652-1655.
Han, et al., "Quantum-dot-tagged microbeads for multiplexed optical coding of biomolecules", Nature Biotechnology, Jul. 2001, vol. 19, pp. 631-635.
Helgeson et al., "Hydrogel Microparticles From Lithographic Processes: Novel Materials for Fundamental and Applied Colloid Science", Current Opinion in Colloid & Interface Science, 16: 106-117 (Apr. 2011).
International Preliminary Report on Patentability by International Bureau of WIPO for International Patent Application No. PCT/US2014/029527 dated Sep. 15, 2015.
International Preliminary Report on Patentability by the International Bureau of WIPO for International Patent Application No. PCT/US2014/029487 dated Sep. 15, 2015.
International Search Report and Written Opinion by International Searching Authority for International Application PCT/US2014/029487 dated Jul. 21, 2014 (10 pages).
International Search Report and Written Opinion by International Searching Authority for International Application PCT/US2014/029527 dated Oct. 9, 2014 (12 pages).
Kang et al. "Digitally tunable physicochemical coding of material composition and topography in continuous microfibres", Nature Materials, Nov. 2011, vol. 10, pp. 877-883.
Kim et al., "Fabrication of low-cost submicron patterned polymeric replica mold with high elastic modulus over a large area", Soft Matter, 8, pp. 1184-1189 (Nov. 28, 2011).
Lee et al., "Colour-barcoded magnetic microparticles for multiplexed bioassays", Nature Materials, Letters, Sep. 2010, vol. 9, pp. 745-749.

(56) References Cited

OTHER PUBLICATIONS

Li Chunxia et al., "Upconversion nanoparticles for sensitive and in-depth detection of Cu2+ ions", Nanoscale, 4 (19), pp. 6065-6071 (Aug. 6, 2012).
Lin et al., "Submicrometre geometrically encoded fluorescent barcodes self-assembled from DNA", Nature Chemistry, Oct. 2012, vol. 4, pp. 832-839.
Mahalingam, et al., "Colloidal Tm3+/Yb3+-Doped LiYF4 Nanocrystals: Multiple Luminescence Spanning the UV to NIR Regions via Low-Energy Excitation", Advanced Materials, Jun. 29, 2009, vol. 21, pp. 4025-4028.
Mandecki et al., "Light-Powered Microtransponders for High Multiplex-Level Analyses of Nucleic Acids", appears as Chapter 4 in Microfabricated Sensors by R. Kordal et al., ACS Symposium Series (Mar. 20, 2002), pp. 57-69.
Mitrelias et al., "Enabling suspension-based biochemical assays with digital magnetic microtags", Journal of Applied Physics, May 11, 2010, vol. 107, pp. 09B319-1 to 09B319-3.
Nicewarner-Pena, et al., "Submicrometer Metallic Barcodes", Science, vol. 294, Oct. 5, 2001, pp. 137-141.
Pregibon et al., "Multifunctional Encoded Particles for High-Throughput Biomolecule Analysis", Science, 315 (5817): pp. 1393-1396 (Mar. 9, 2007).
Vetrone et al., "The Active-Core/Active-Shell Approach: A Strategy to Enhance the Upconversion Luminescence in Lanthanide-Doped Nanoparticles", Adv. Func. Mater. 19: 2924-2929 (Jul. 16, 2009).
Wang et al, "Recent Advances in the Chemistry of Lanthanide-doped Upconversion Nanocrystals," Chemical Society Reviews, 38: 976-989 (Feb. 12, 2009).
Wang, et al., "Simultaneous phase and size control of upconversion nanocrystals through lanthanide doping", Nature, Letters, Feb. 25, 2010, vol. 463, pp. 1061-1065.
Wang, et al., Upconversion Multicolor Fine-Tuning: Visible to Near-Infrared Emission from Lanthanide-Doped NaYF4 Nanoparticles, Journal American Chemical Society, 2008, vol. 130, pp. 5642-5643.
Yan, Bin, et al. "Near infrared light triggered release of biomacromolecules from hydrogels loaded with upconversion nanoparticles." Journal of the American Chemical Society 134 (40) (Sep. 26, 2012): 16558-16561.
Zhang et al., "Fluorescence upconversion microbarcodes for multiplexed biological detection: nucleic acid encoding", Advanced Materials, 23 (33), pp. 3775-3779 (Sep. 2011). (6 pages).
Zhang et al., "Rare-Earth Upconverting Nanobarcodes for Multiplexed Biological Detection", Small, 7(14): pp. 1972-1976 (Jul. 4, 2011).
Zhao, et al., "Microfluidic Generation of Multifunctional Quantum Dot Barcode Particles", Journal of the American Chemical Society, May 16, 2011, vol. 133, pp. 8790-8793.
Zhao, et al., "Multifunctional photonic crystal barcodes from microfluidics", NPG Asia Materials, Sep. 7, 2012, 4, e25; doi:10.1038/am. 212.46.
Wang et al., Semiconductor Quantum Dot-Labeled Microsphere Bioconjugates Prepared by Stepwise Self-Assembly. Nano Letters. 2002;2(8):857-861.
Wilson et al., Encoded microcarriers for high-throughput multiplexed detection. Angew Chem Int Ed Engl. Sep. 18, 2006;45(37):6104-17.
Yang et al., Layer-by-Layer Construction of Novel Biofunctional Fluorescent Microparticles for Immunoassay Applications. J Colloid Interface Sci. Feb. 15, 2001;234(2):356-362.
European Search Report for Application No. 17177965.5, dated Apr. 6, 2018. 11 pages.

* cited by examiner

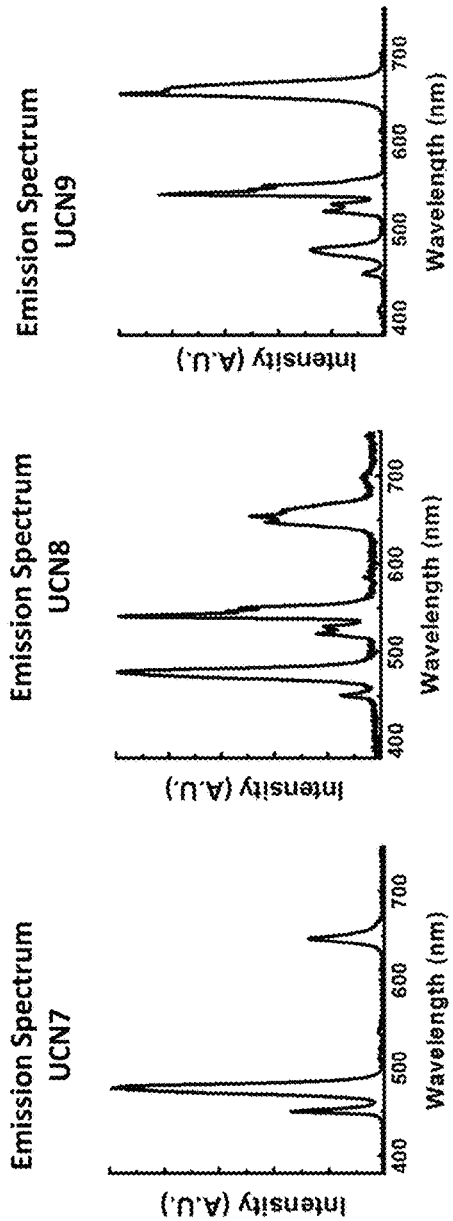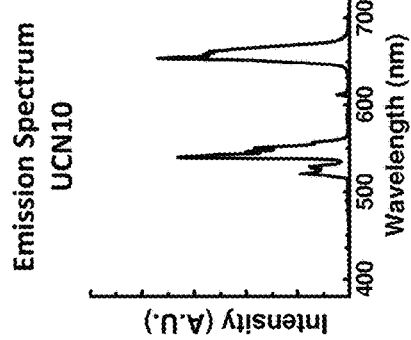

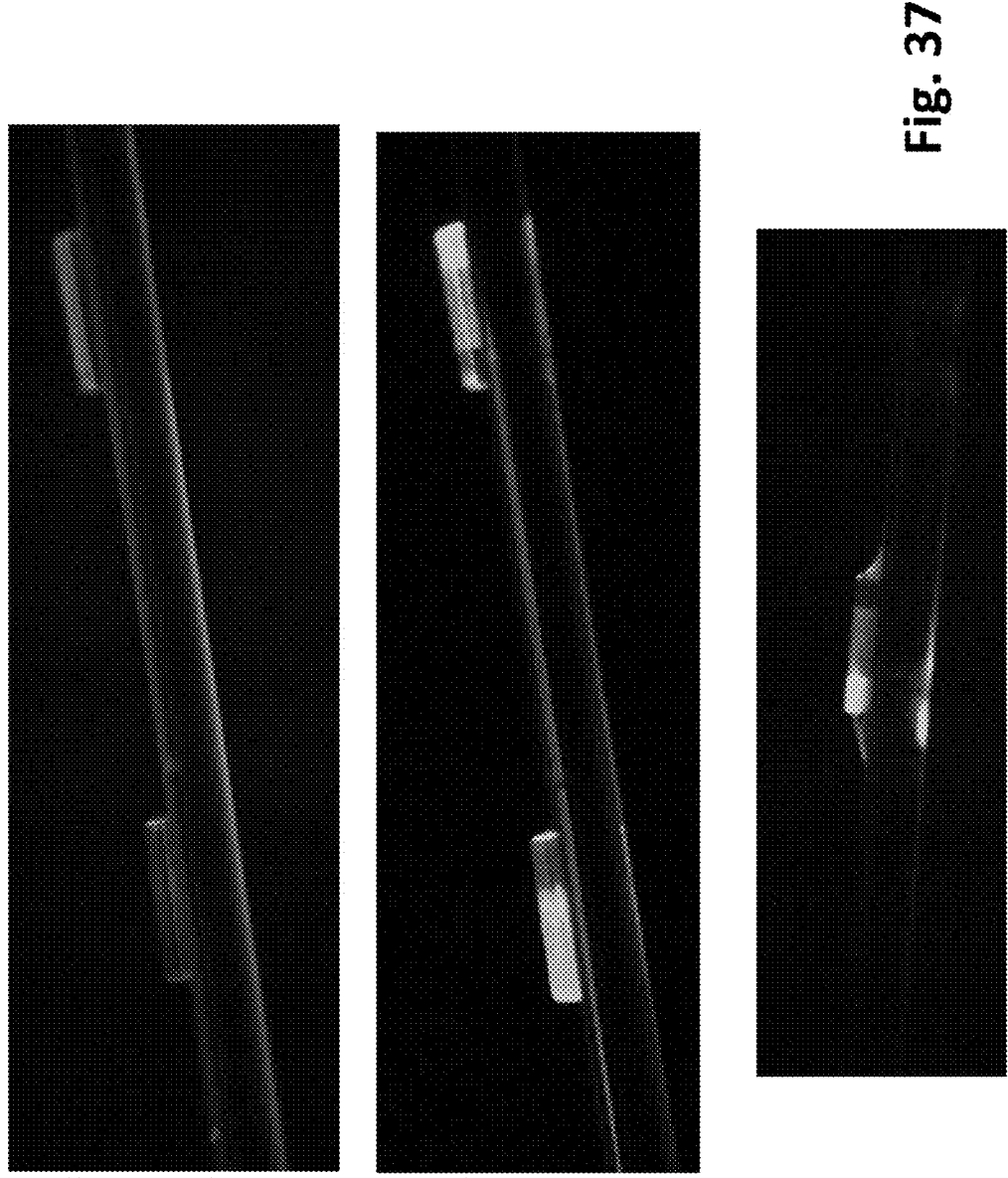

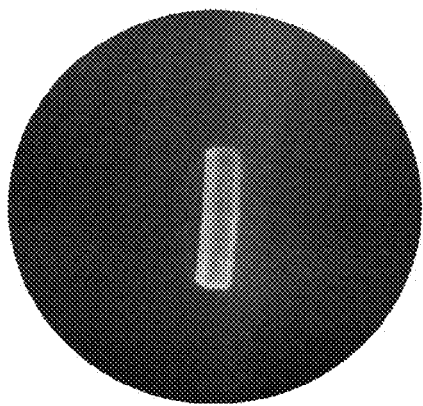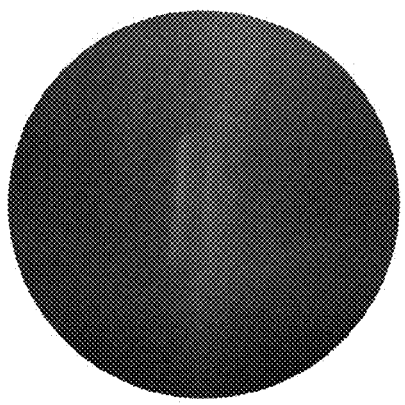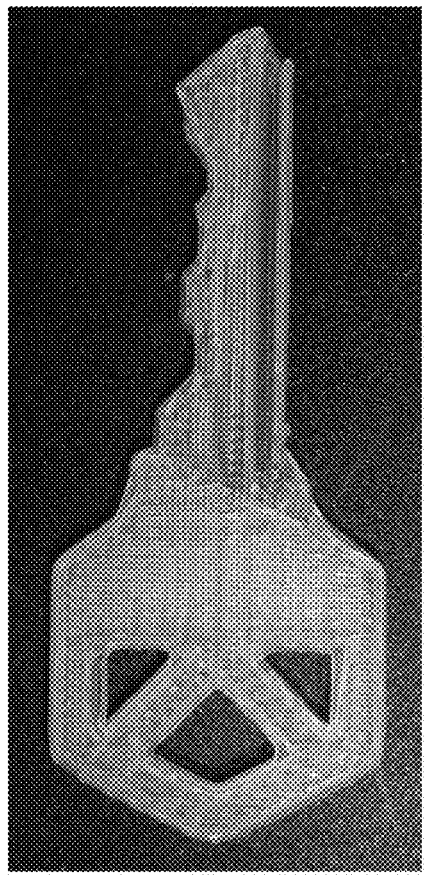
Fig. 39

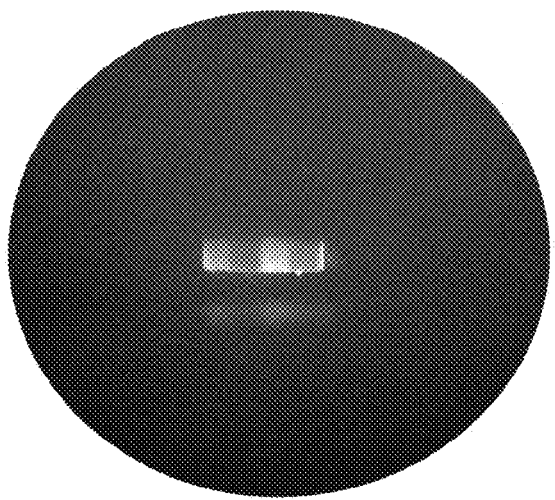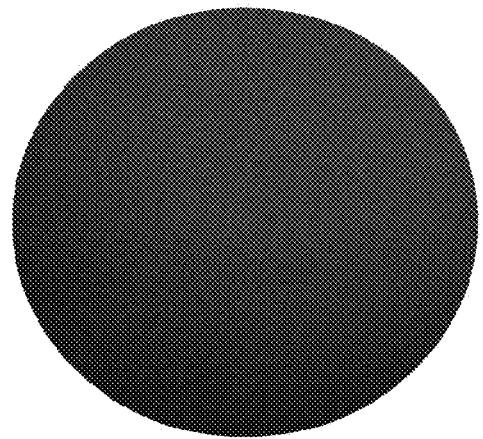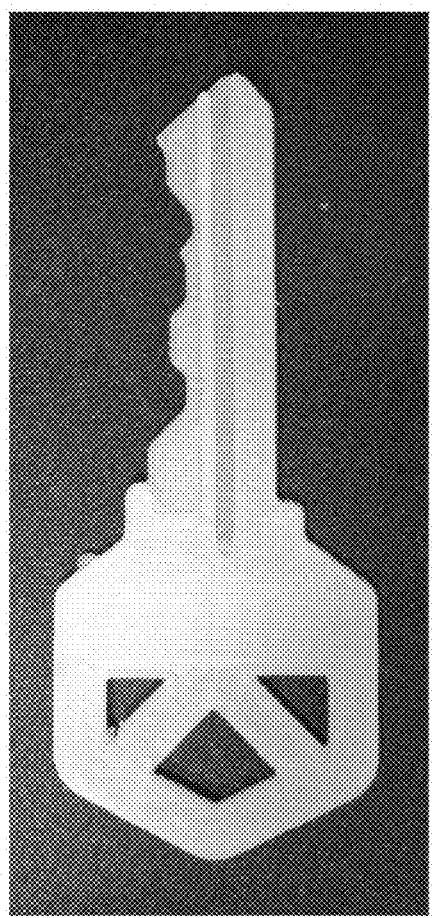
Fig. 40

RARE EARTH SPATIAL/SPECTRAL MICROPARTICLE BARCODES FOR LABELING OF OBJECTS AND TISSUES

RELATED APPLICATIONS

The present application claims benefit of, and priority to U.S. patent application Ser. No. 14/214,528, filed Mar. 14, 2014, which claims priority to U.S. Provisional Patent Application No. 61/801,351, filed Mar. 15, 2013, and U.S. Provisional Patent Application No. 61/800,995, filed Mar. 15, 2013, all of the above applications being herein incorporated by reference in their entirety.

STATEMENT OF GOVERNMENT INTEREST

This invention was made with government support under Contract No. FA8721-05-C-0002 awarded by the U.S. Air Force and under Grant Nos. DMR-1006147 and CMMI-1120724 awarded by the National Science Foundation. The government has certain rights in the invention.

BACKGROUND

Many industries (e.g., pharmaceuticals, banks, fine art) are interested in labeling of objects with labels that are resistant to "spoofing" or counterfeiting. There are currently many different technologies for labeling objects with codes, such as one-dimensional barcodes (e.g., UPC barcodes), two-dimensional codes (e.g., QR codes), and radio frequency identification (RFID) tags. However, there is a need for smaller, more unobtrusive labeling that is resistant to "spoofing" or counterfeiting.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8 is a graph of an emission spectrum of exemplary UCNs labeled "UCN7", in accordance with an embodiment.

FIG. 9 is a graph of an emission spectrum of exemplary UCNs labeled "UCN8", in accordance with an embodiment.

FIG. 10 is a graph of an emission spectrum of exemplary UCNs labeled "UCN9", in accordance with an embodiment.

FIG. 11 is a graph of an emission spectrum of exemplary UCNs labeled "UCN10", in accordance with an embodiment.

FIG. 37 shows luminescence images of microparticles labeling a thread, in accordance with an embodiment.

FIG. 39 is an image of encoded microparticles embedded in the bulk of a PVA key, in accordance with an embodiment.

FIG. 40 is an image of encoded microparticles embedded in the bulk of an ABS key, in accordance with an embodiment.

Figure 1:
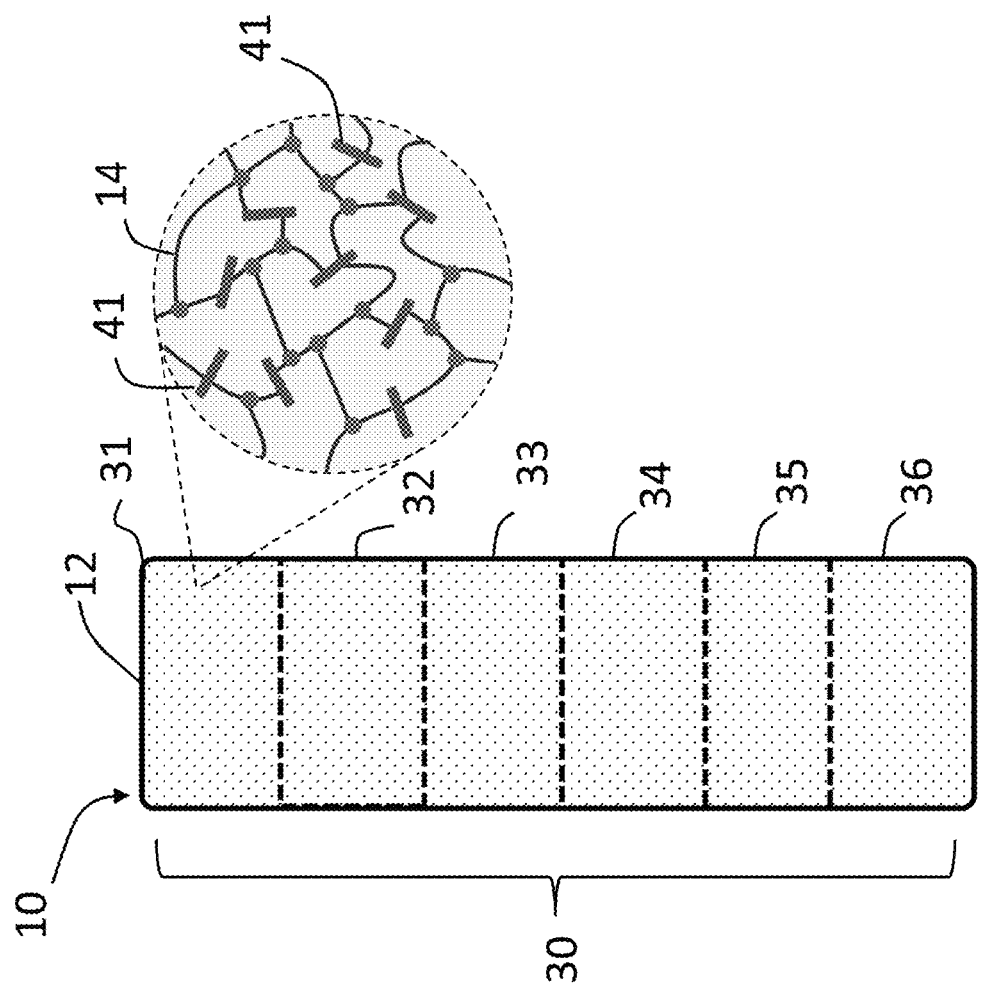
FIG. 1 schematically depicts an exemplary microparticle, in accordance with an embodiment.
Figure 2:
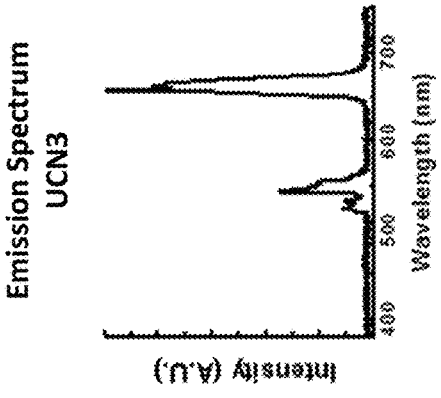
FIG. 2 is a graph of an emission spectrum of exemplary upconversion nanocrystals (UCNs) labeled "UCN1", in accordance with an embodiment.
Figure 3:
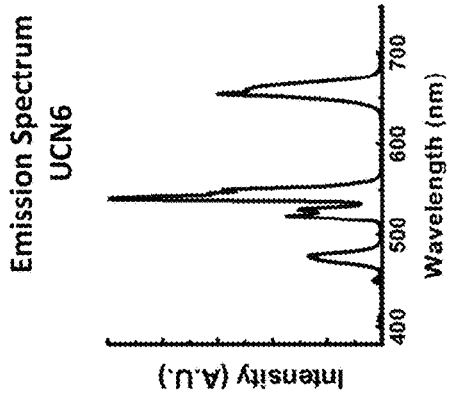
FIG. 3 is a graph of an emission spectrum of exemplary UCNs labeled "UCN2", in accordance with an embodiment.
Figure 4:
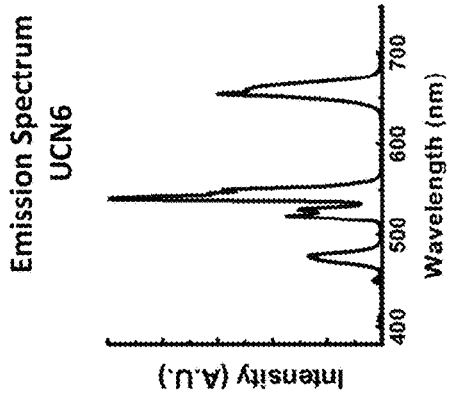
FIG. 4 is a graph of an emission spectrum of exemplary UCNs labeled "UCN3", in accordance with an embodiment.
Figure 5:
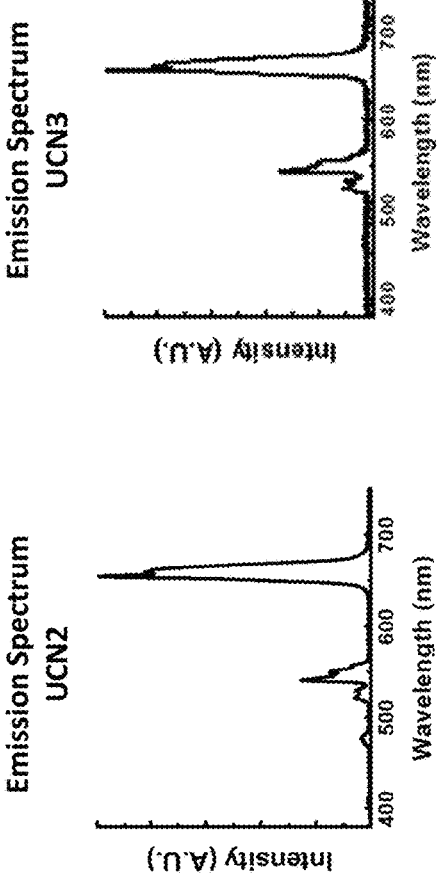
FIG. 5 is a graph of an emission spectrum of exemplary UCNs labeled "UCN4", in accordance with an embodiment.
Figure 6:
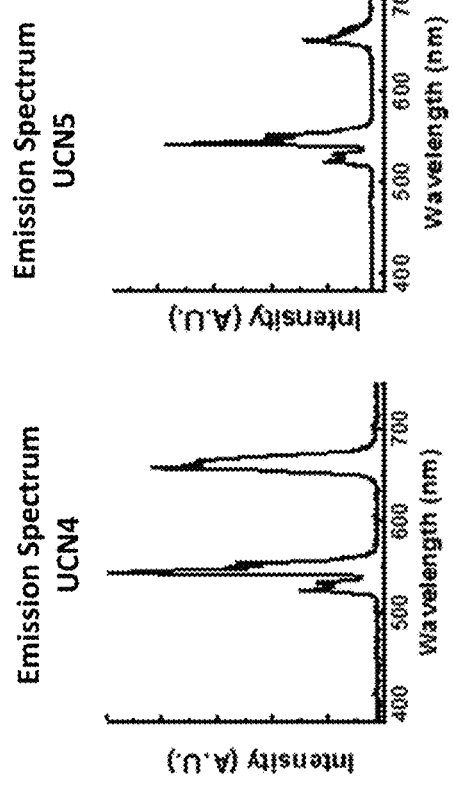
FIG. 6 is a graph of an emission spectrum of exemplary UCNs labeled "UCN5", in accordance with an embodiment.
Figure 7:
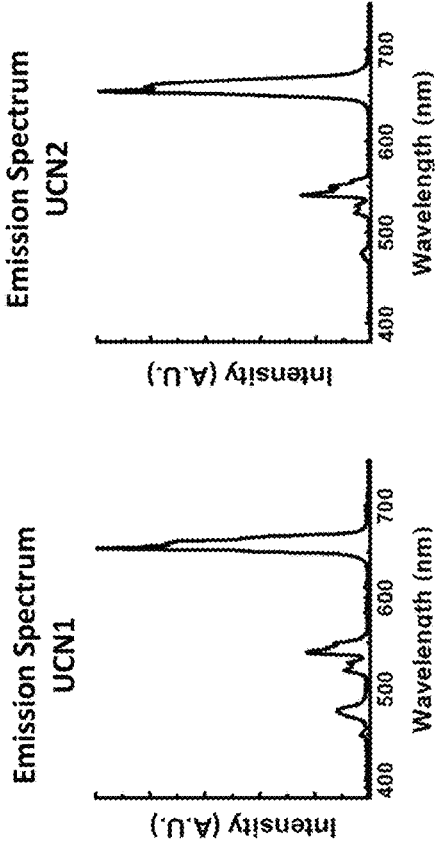
FIG. 7 is a graph of an emission spectrum of exemplary UCNs labeled "UCN6", in accordance with an embodiment.

Additional features, functions and benefits of the disclosed methods, systems and media will be apparent from the description which follows, particularly when read in conjunction with the appended figures.

DETAILED DESCRIPTION

There are many challenges for labeling objects with labels that are resistant to counterfeiting or spoofing. For example, unique encoding of single units within information-intensive processes like pharmaceutical packaging may entail encoding capacities of $10^5$-$10^{12}$ and high-throughput particle synthesis. As another example, exposure to harsh environments for some applications requires thermal insensitivity, biocompatibility and/or chemical resistance. The complexity and cost of readout systems for some labeling technologies can limit implementation. Some labeling applications require low-error readout in the presence of confounding factors (e.g. complex background, obscurants, noise), which is a difficult technical challenge.

Embodiments include polymer microparticles for labeling of articles and/or tissues, methods of producing the microparticles, and methods of labeling using the microparticles. Each hydrogel microparticle includes an encoded region. The encoded region includes multiple portions with one or more of the portions including an associated plurality of upconversion nanocrystals (UCNs) with a distinct spectral signature. The multiple portions of the encoding region enable spatial encoding of the microparticle. The associated plurality of UCNs for each region is selected from a set of spectrally distinguishable UCNs, which enables spectral encoding for each portion of the microparticle. By combining spatial and spectral encoding, the microparticles have massive multiplexing capabilities with superior scaling capability.

The coding scales exponentially as $C^S$ for asymmetric particles and as $C^S/2$ for symmetric particles, where C is the number of distinguishable spectral signatures (UCN 'col-ors') and S is the number of spatial features (e.g., microparticle 'stripes'). For example, for a symmetric microparticle with S encoding portions and a set of C different spectrally distinguishable nanocrystals, the following equation lists the number of codes or unique identifiers that would be available:

$$\sum_{x=0}^{S-1} C^{(S-x)}$$

For example, about 20,000 unique identifiers/codes can be generated for a system in which the encoding region of symmetric microparticles has six portions and each portion includes a plurality of UCNs selected from a set of five different types of spectrally distinct nanocrystals. As another example, about 500,000 unique identifiers/codes can be generated for a system in which the encoding region of the symmetric microparticle has six portions and each portion includes a plurality of UCNs selected from a set of nine different types of spectrally distinct nanocrystals. Thus, a modest number of colors may be coupled with a similarly modest number of stripes to yield considerable encoding capacities that scale rapidly with incremental changes to either quantity. To increase the labeling capacity, asymmetric microparticles could be employed. For example, an asymmetric microparticle with six portions with each portion including one of nine different types of spectrally distinct nanocrystals would produce over a million unique identifiers/codes. To increase the labeling capacity, a combination of multiple microparticles could be used to label an object.

Some embodiments combine spatial patterning with rare-earth upconversion nanocrystals (UCNs), single wavelength near-infrared excitation and portable charge-coupled device (CCD)-based decoding to distinguish particles synthesized by means of flow lithography. Some embodiments exhibit large, exponentially scalable encoding capacities (>$10^6$), an ultralow decoding false-alarm rate (<$10^{-9}$), the ability to manipulate particles by applying magnetic fields, and dramatic insensitivity to both particle chemistry and harsh processing conditions. Experiments conducted by the inventors show quantitative agreement between observed and predicted decoding for a range of practical applications with orthogonal requirements, including covert multiparticle barcoding of pharmaceutical packaging (refractive-index matching), multiplexed microRNA detection (biocompatibility) and embedded labeling of high-temperature cast objects (temperature resistance).

Some embodiments employ a robust encoding method for compatibility with high-throughput particle synthesis and portable CCD-based decoding. In some embodiments, the resulting particles and decoding system exhibit dramatic insensitivity to particle chemistry—enabling tuning of encoding capacity and decoding error rate independently of particle material properties—as well as the capacity for straightforward magnetic manipulation. In the example described below, the inventors demonstrate quantitatively predictable decoding of both temperature-resistant and biocompatible particles in challenging, realistic environments. With single-particle encoding capacities in excess of 1 million and error rates of less than 1 part per billion (ppb), some embodiments expand the practically accessible number of codes for applications like forensic product labeling and multiplexed bioassays by orders of magnitude. Methods described herein may be employed to extend the use of encoded particles to a broad and evolving range of previously unexplored industrial applications. Embodiments may be employed to produce covert, durable anti-counterfeiting labels with massive encoding capacity from small sets of uniquely encoded particles.

FIG. 1 schematically depicts an exemplary microparticle 10 that can be used for labeling an article or a tissue, in accordance with an embodiment. The microparticle 10 has a body 12 including a polymer 14. The body 12 has an encoded region 30 that includes multiple different portions (e.g., portions 31, 32, 33, 34, 34, 35, 36) with each portion (31-36 having an associated plurality of upconversion nanocrystals (UCNs) (e.g., UCN 41) selected from a set of spectrally distinguishable UCN (see discussion accompanying FIGS. 2-11 below). In some embodiments, one or more portions may not include any nanocrystals and may serve as a "blank" or null portion for encoding.

For example, in some embodiments, a first plurality of UCNs with a first spectral signature is disposed in a first portion 31 of the encoded region. A second portion 32 of the encoded region includes a second plurality of UCNs with a second spectral signature different than the first spectral signature. In some embodiments, the encoded region of the microparticle also includes a third portion 33 having a third plurality of UCNs. In some embodiments, the encoded region of the microparticle also includes a fourth portion 34 having a fourth plurality of UCNs. In some embodiments, the encoded region of the microparticle also includes a fifth portion 35 having a fifth plurality of UCNs. The plurality of microparticles in each portion (31-36) of the encoded region is selected from a set of spectrally distinguishable UCNs.

One of ordinary skill in the art in view of the present disclosure would recognize that each microparticle may include an encoding region with fewer than six portions and associated pluralities of UCNs (e.g., five portions, four portions, three portions, two portions) or more than six portions and associated pluralities of UCNs (e.g., portions, seven portions, eight portions, nine portions, ten portions, etc.).

The spectral signature associated with a plurality of UCNs disposed in a portion of the encoded region is also referred to herein as the spectral signature of the portion of the encoded region. In some embodiments, two or more portions of the encoded region may have the same spectral signature. In some embodiments, two or more portions of the encoded region with the same spectral signature may be adjacent to each other. In some embodiments, any portions of the encoded region with the same spectral signature must be separated from each other by one or more portions of the encoded region having different spectral signature(s). In some embodiments, each portion of the encoded region must have a spectral signature different from that of every other portion of the encoded region. In some embodiments, one or more portions of the encoded region do not include nanocrystals so that the portion or portions is "blank" without a spectral signature. The spectral signature of a UCN includes information associated with the emission spectrum of the UCN that distinguishes it from another type of nanocrystal. In some embodiments, the spectral signature of a UCN or of a plurality of similar UCNs may include the integrated intensity of emission of one spectral band (or emission in one spectral range) versus another spectral band (or emission in another spectral range). A spectral signature or information regarding a spectral signature may be referred to herein as a spectral code.

FIGS. 2-10 show emission spectra for an example set of nine spectrally distinguishable types of UCNs, labeled UCN1-UCN9 respectively, when excited with near infrared (NIR) light (e.g., 980 nm light from an NIR diode laser). UCNs in the example set luminesce in multiple narrow bands (e.g., bands less than 70 nm wide at full width half maximum (FWHM)) in the visible range when exposed to lower frequency (e.g., near infrared (NIR)) light. Specifically, the example set of spectrally distinguishable UCNs (e.g., UCN1-UCN10) emit in two or more bands centered around 470 nm (e.g., 445-500 nm), centered around 550 nm (e.g., 520-560 nm), and centered around 650 nm (e.g., 640-670 nm). For simplicity, the 445-500 nm band is referred to herein as the blue band, the 520-560 nm band is referred to herein as the green band, and the 640-670 nm band is referred to herein as the red band.

One of ordinary skill in the art in view of the present disclosure would recognize that the set of UCNs may include fewer than nine (e.g., eight, seven, six, five, four, three, two) or more than nine (e.g., ten, eleven, twelve, etc.) different types of spectrally distinguishable UCNs. Further, one of skill in the art in view of the present disclosure would recognize that UCNs having different spectra than those shown, and UCNs than emit in different bands than those shown, also fall within the scope of embodiments. For example, FIG. 11 shows an emission spectrum for a UCN labeled UCN10 that may be used in the set as an alternative to any of UCN1-UCN9 or in addition to UCN1-UCN9. To augment encoding capacity, the palette of spectrally distinct UCNs may be further expanded by adjusting Yb—Er—Tm ratios with negligible impact on the decoding error rate.

The spectral signature of a plurality of UCNs may include information related to the ratio or ratios of the integrated intensities emitted in various bands (e.g., the ratio of the red band to the green band or vice versa, the ratio of the red band to the blue band or vice versa, the ratio of the blue band to the green band or vice versa, or any combination of the aforementioned). These ratios can be defined with respect to the emission spectra of the UCNs. However, in some embodiments, the spectral signature of a plurality of UCNs may include both information regarding the intensity of light emitted in various bands and include information regarding the responsivity of the detector or image sensor to be used. Any detector, image sensor, or imaging device may be employed. For example, the detector or imaging device may be a charge-coupled device (CCD), a photomultiplier tube-based device (PMT), a complementary metal-oxide-semiconductor (CMOS) imaging sensor, an avalanche photodiode array (APD) imaging device, etc. In some embodiments, an imaging sensor with more than one color channel may be employed.

Figure 13:
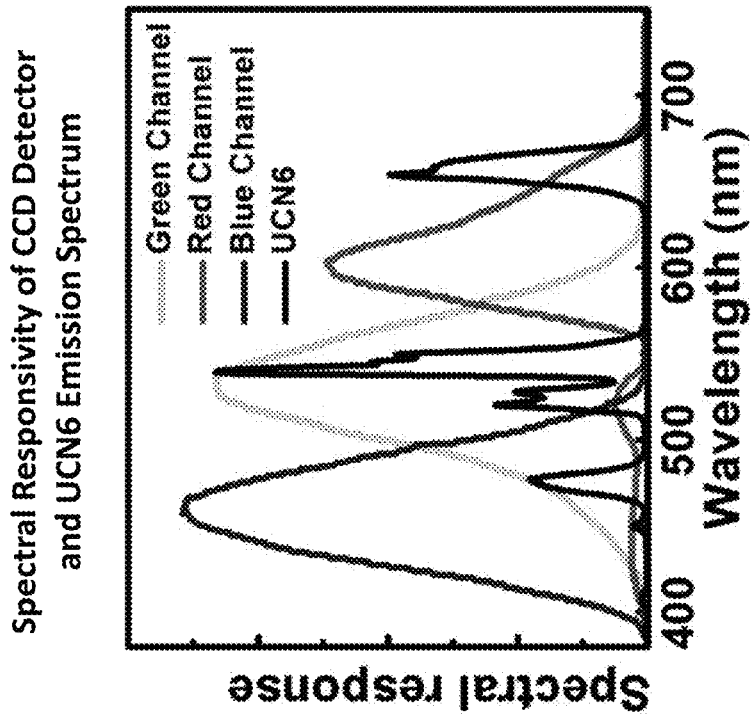
FIG. 13 is a graph of the emission spectrum of UCN6 overlaying the spectral responsivity of RGB channels of a CCD image sensor, in accordance with an embodiment.
Figure 12:
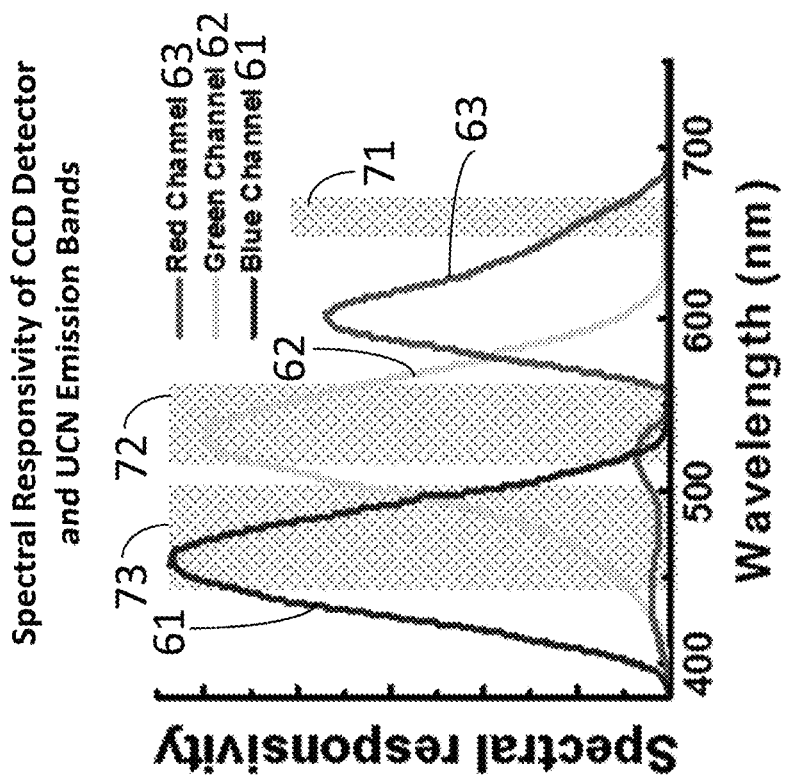
FIG. 12 is a graph of spectral responsivity of RGB channels of a CCD image sensor with UCN emission bands overlaid, in accordance with an embodiment.

FIG. 12 shows the spectral responsivity of red 61, green 62 and blue 63 channels for a typical RGB CCD device that may be used as a detector in some embodiments. As shown, the red 71, green 72, and blue 73 emission bands of the exemplary set of UCNs overlap the spectral responsivities of the respective red 61, green 62, and blue 63 channel responsivity curves. For example, FIG. 13 shows the emission spectrum of UCN6 overlaying the spectral responsivity of channels of a typical RGB device. A convolution of the emission spectrum with the expected spectral responsivity for each image sensor channel yields curves corresponding to the expected spectral response of each channel of the CCD image sensor to each type of UCN. The spectral signature for a type of UCNs can include information regarding the expected spectral response of an image sensor to a specific UCN emission spectrum, such as a ratio of the expected integrated intensity detected for two color channels.

For example, Table 1 below shows the expected spectral response of a CCD device to the emission spectra of the UCN3-UCN7 and UCN10 types of UCNs (see FIGS. 4-8 and 11 above for emission spectra). The expected spectral response is a convolution of the emission spectrum for type of UCN with the image sensor channel spectral responsivity shown in FIG. 12. Specifically, Table 1 shows the expected integrated total intensity for each color channel due to emission of the UCNs. Table 1 also includes ratios for the expected total intensity for the green channel to the red channel, for the blue channel to the red channel, and for the blue cannel to the green channel. Expressing the integrated intensities as ratios for different color channels reduces or eliminates the need for calibration to determine the absolute intensity for any particular color channel or emission band.

TABLE 1

| Type | Expected Integrated Intensity* R Channel | Expected Integrated Intensity G Channel | Expected Integrated Intensity B Channel | Channel Ratio G/R | Channel Ratio B/R | Channel Ratio B/G |
|---|---|---|---|---|---|---|
| UCN3 | 163.4 | 86.3 | 0 | 0.528 | 0 | 0 |
| UCN4 | 225.4 | 197.5 | 0 | 0.876 | 0 | 0 |
| UCN5 | 91.9 | 164.5 | 0 | 1.790 | 0 | 0 |
| UCN7 | 24.7 | 52.1 | 219.9 | 2.109 | 8.9 | 4.220 |
| UCN6 | 138.5 | 158.1 | 120.4 | 1.141 | 0.869 | 0.7609 |
| UCN10 | 161.6 | 131.5 | 0 | 0.814 | 0 | 0 |

Recent technologies have employed microparticles including fluorescent coding for biochemical or chemical assays. The inventors have found that employing UCNs for identifying different encoded regions of a microparticle has many benefits when compared with other techniques currently used for encoding microparticles. For example, some other techniques employ one-dimensional or two-dimensional thickness variations or holes in a fluorescently labeled coded region of a microparticle for identification.

In contrast with UCNs having multiple narrow emission bands, commonly used fluorescent labeling molecules (e.g., fluorophores) each tend to emit in a single broad band (e.g., DAPI fluorescent dye has a single emission band that is about 100 nm wide FWHM). In microparticles using fluorophores for encoding, the broad emission bands of the fluorophores limits the number of different fluorophores that may be employed without having significant overlap between emission bands and resulting ambiguity in identification. In addition, the absence of multiple emission bands for a single fluorophore may require the use of an external calibration standard. In contrast, UCNs have multiple narrow emission bands in different portions of the visible spectrum (e.g., separated by tens to hundreds of nm). The ratio of intensity of emission in various bands can be used to distinguish between different nanocrystals, and also acts as an internal calibration standard, obviating the need for external calibration.

Microparticles using UCNs for encoding may experience less reduction of the signal to noise ratio due to autoluminescence than microparticles using fluorophores for encoding. Luminescent UCNs absorb light in one range of wavelengths and emit light in a shorter range of wavelengths (e.g., absorb in the NIR range and emit in the visible range). In contrast, commonly used fluorophores and quantum dots usually absorb light in a wavelength range and emit light in a longer wavelength range (e.g., absorbing in the ultraviolet range and emitting in the visible range). For example, the commonly used fluorophore 4',6-diamidino-2-phenylindole (DAPI) has absorption maximum around 370 nm (UV) and an emission maximum around 450 nm (blue). Illumination of the fluorophores for identification (e.g., with UV light) may result in unintended autofluorescence of materials and solvents in the visible wavelengths that decreases the signal to noise ratio, which can be a significant problem with biological samples. Because the nanocrystals described herein are upconverting, the NIR light used to excite the nanocrystals generally does not cause autoluminescence in the shorter wavelengths of the visible range. Thus, the use of UCN may improve the signal to noise ratio for an encoded region.

Microparticles using different types of UCNs for encoding may require only a single narrow band excitation source as opposed to microparticles using different types of fluorophores, which may require multiple light sources to provide excitation in different wavelength bands. For example, a 980 nm light source with a power density of less than 10 W/cm$^2$ (e.g., an near infra-red (NIR) laser diode) may be used as a single excitation source for multiple different types of UCNs. In contrast, microparticles using common fluorophores for parts of the visual light spectrum, such as DAPI (blue), Oregon green 500 (green) and ALEXA FLUOR 633 (red) with absorption maximums at 350 nm, 503 nm and 632 nm, respectively, may require multiple different excitation sources such as a UV laser, an argon-ion laser, and a red helium-neon laser.

In some embodiments, the UCNs are rare-earth nanocrystals that are bright anti-Stokes emitters with tunable spectral properties. Individual UCNs absorb continuous-wave (CW) NIR light at a single wavelength and emit in multiple narrow bands of the visible spectrum. Large anti-Stokes shifts reduce spectral interference from sample autofluorescence and lead to enhanced signal-to-noise ratios. In contrast to M-ink (an optically active dye in which nanostructured magnetic materials reflect different wavelengths of light) or quantum dots, these benefits persist even in the presence of obscurants or a complex reflective background. Tuning of emission intensities in multiple bands by adjusting relative stoichiometries of lanthanide dopants permits ratiometrically unique spectral encoding, in which the ratio of integrated intensities in two or more bands serve as the code, rather than absolute intensity. In some embodiments, external spectral standards (e.g., as required by porous silicon crystals), precise dye loading (e.g., as used with quantum dots and luminex), sensitive instrumentations (e.g. as required by M-Ink), and extensive calibration may be unnecessary for readout, enabling the use of standard CCD imaging for decoding.

Example Synthesis of UCNs

Lanthanide-doped NaYF$_4$ UCNs were made via a scalable batch hydrothermal synthesis, which is only one of numerous known protocols for synthesis of NaYF$_4$ UCNs.

Aqueous rare-earth chloride salts, sodium hydroxide, ammonium fluoride, ethanol and oleic acid were heated in a TEFLON-coated stainless steel pressure vessel. Specifically, 2 ml of ReCl$_3$ (0.4 M, RE=Y, Yb, Er, Gd, Tm) and 2 ml of NH$_4$F (2 M) were added to a mixture of 3 ml of NaOH (0.6 M), 10 ml of ethanol and 10 ml of oleic acid. The solution was transferred to a 50 ml TEFLON-lined autoclave and heated at 200° C. for 2 hours. The resulting products were centrifuged to collect the nanocrystals, which were then repeatedly washed with ethanol and deionized water, and then re-dispersed in cyclohexane.

During synthesis, the inventors used the concentration of various lanthanide dopants and the reaction time and temperature to improve the luminescence intensity of the nanocrystals and to alter the upconversion spectrum of the nanocrystals.

The synthesis procedure described above can produce $NaYF_4$ UCNs in two different phases having different crystal structures: an α-phase with a cubic crystal structure and a β-phase with a hexagonal crystal structure. Generally speaking, luminescence intensity is significantly higher in β-phase crystals than in α-phase crystals due to the lower ratio of surface defects to crystal volume in the β-phase. Without high levels of gadolinium doping, relatively high temperatures must be maintained for relatively long times (e.g., 350° C. for 24 hours) to induce the α→β phase transition in the nanocrystals. In contrast, the inventors doped with 30 mol % gadolinium (Gd) to induce the α→β phase transition at a lower temperature (200° C.) held for a shorter time (2 hours). The Gd has little to no effect on the shape of the upconversion emission spectrum generated due to the presence of the other dopants.

Increasing reaction time and increasing reaction temperature tended to increase the luminescence intensity of the UCNs due to increased nanocrystal size. Increasing the nanocrystal size decreases the ratio of surface area to volume for the nanocrystals, thereby decreasing the ratio of surface defects to crystal volume. Further, luminescence for larger nanocrystals was less likely to be red-shifted due to preferential quenching of high frequency emission, which can occur in smaller nanocrystals.

Figure 14:
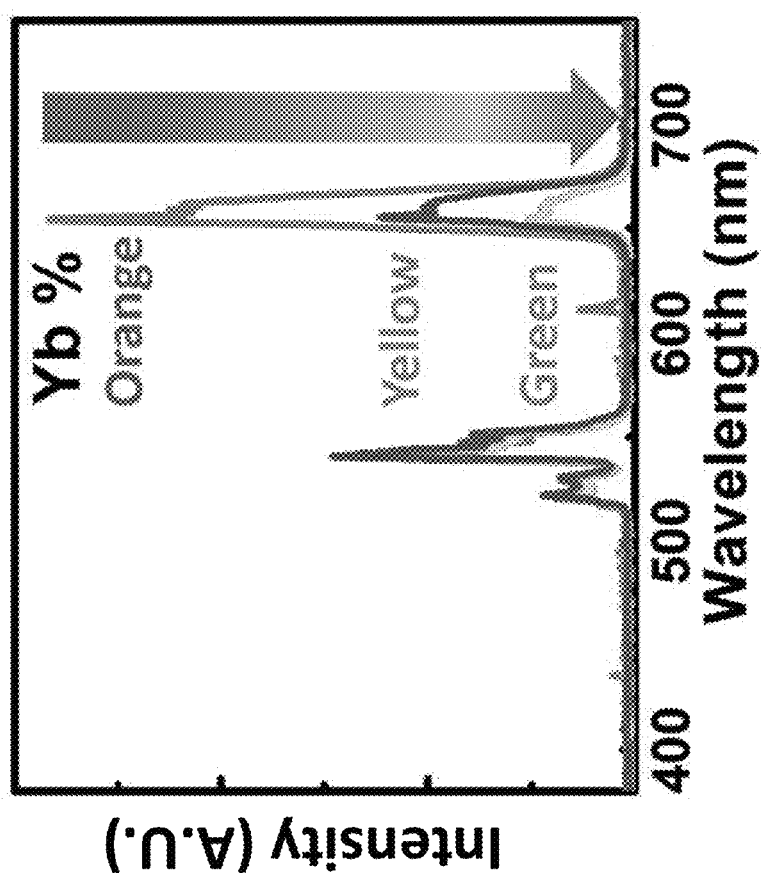
FIG. 14 is a graph showing unique upconversion emission spectra produced by varying dopant concentrations, in accordance with an embodiment.

The concentrations of dopants other than Gd were used to change the upconversion emission spectrum. Spectrally distinct UCN were produced by adjusting the relative stoichiometries of the lanthanide ions $Yb^{3+}$, $Er^{3+}$ and $Tm^{3+}$ in the UCN reaction premix. The lanthanide dopant stoichiometries have relatively little impact on the UCN nanostructure and surface chemistry, decoupling control of the emission spectrum from the particle chemistry and resulting material properties. Ytterbium ($Yb^{3+}$) is an important dopant for bright multicolor emission, because it acts as a high-NIR absorption cross-section absorption and energy transfer agent for upconverting emission. Increasing the Yb percentage tends to 'red-shift' the upconversion spectrum, increasing the ratio of the emission intensity in the red band (640-670 nm) relative to the emission intensity in the green band (520-560 nm) in Erbium ($Er^{3+}$) co-doped crystals. FIG. 14 illustrates how increasing the Yb concentration shifts the emission spectrum and shifts overall emission color from green to orange. Doping with $Er^{3+}$ at low levels (2% or less) leads to narrow peaks centered at 550 nm and 650 nm. Overall emission color for materials doped with $Yb^{3+}$ and $Er^{3+}$ can range from green to red, depending on the Yb concentration. Doping with Thulium ($Tm^{3+}$) at very low levels (0.2%) leads to emission in the blue band (445-500 nm) and a more intense peak at 800 nm.

Figure 15:
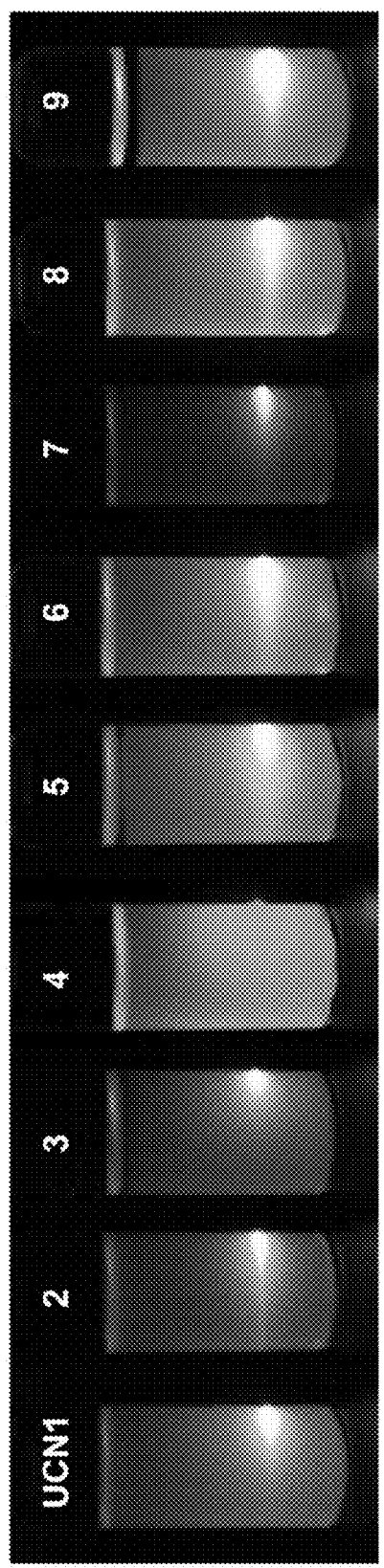
FIG. 15 is an image of different types of UCNs under NIR illumination, in accordance with an embodiment.

Ten different types of spectrally distinguishable lanthanide-doped $NaYF_4$ UCNs labeled UCN1-UCN10 were produced. The spectra of the different types of lanthanide-doped $NaYF_4$ UCNs appear in FIGS. 2-11. The overall colors of the UCN1-UCN9 types when irradiated with an NIR laser diode are shown in FIG. 15, which includes a luminescence image of suspensions of UCN1-UCN9 in cyclohexane upon 980 nm near infra-red (NIR) excitation. As illustrated by FIG. 15, the colors of the UCNs can be readily distinguished by the naked eye. The composition of the dopant used for each type of nanocrystals is listed in Table 2 below. The Y concentration, which makes up the balance of each dopant concentration, is in square brackets because it is not an active dopant.

TABLE 2

| Label | Gd (mol %) | Yb (mol %) | Er (mol %) | Tm (mol %) | [Y (mol %)] | Description of overall color |
|---|---|---|---|---|---|---|
| UCN1 | 30 | 69.7 | 0.1 | 0.2 | [0] | Violet |
| UCN2 | 30 | 69.9 | 0.1 | — | [0] | Red |
| UCN3 | 30 | 68 | 2 | — | [0] | Orange |
| UCN10 | 30 | 40 | 2 | — | [28] | Dark Yellow |
| UCN4 | 30 | 30 | 2 | — | [38] | Yellow |
| UCN5 | 30 | 18 | 2 | — | [50] | Green |
| UCN6 | 30 | 20 | 0.1 | 0.2 | [49.7] | Cobalt |
| UCN7 | 30 | 18 | — | 0.2 | [51.8] | Blue |
| UCN8 | 30 | 18 | 0.03 | 0.2 | [51.77] | Sky Blue |
| UCN9 | 30 | 31.7 | 0.1 | 0.2 | [38] | Grey |

Figure 16:
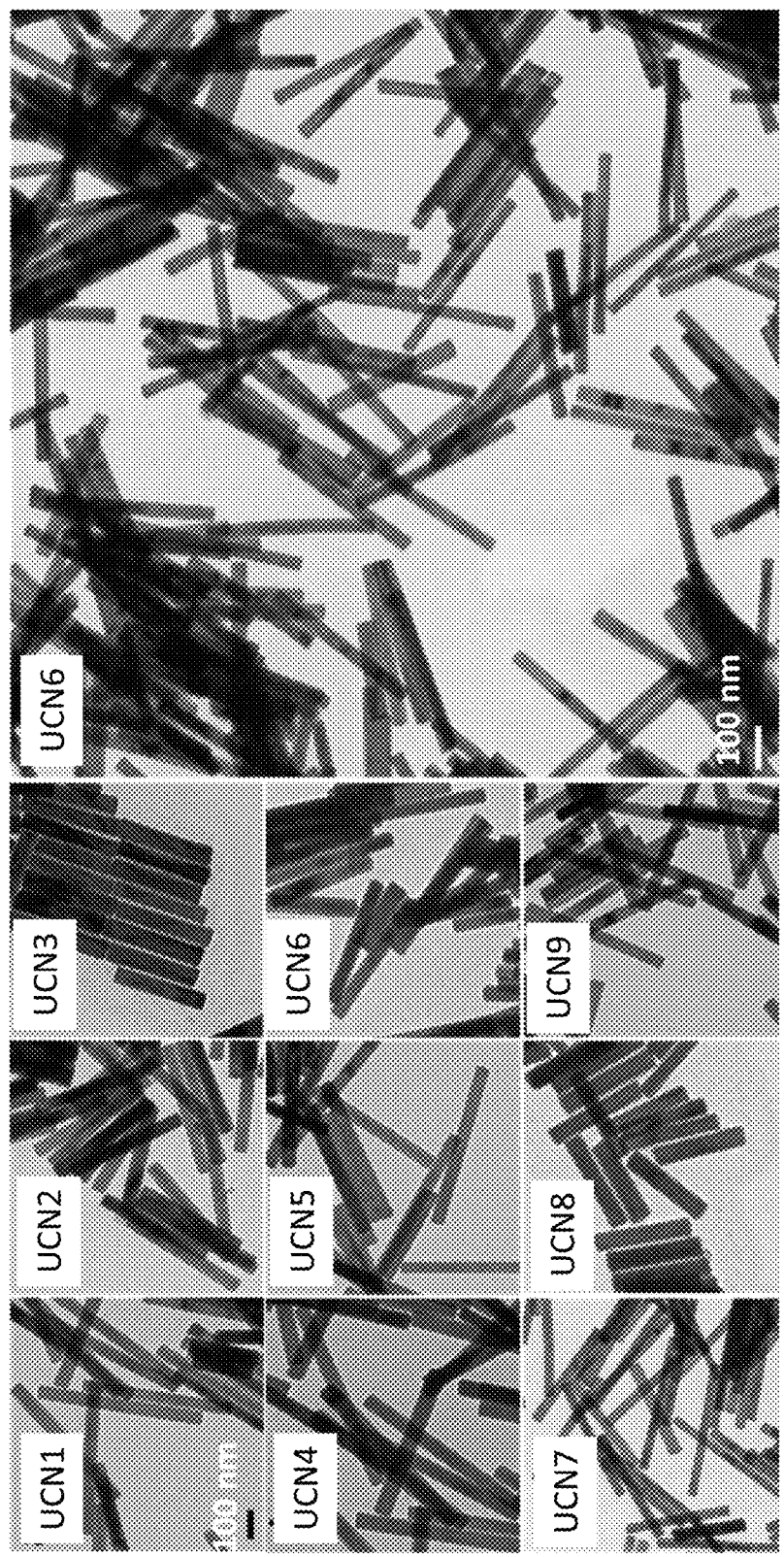
FIG. 16 is a transmission electron micrograph of different types of UCNs, in accordance with an embodiment.

FIG. 16 shows transmission electron microscopy (TEM) images of the UCN1-UCN9 types of UCNs produced by the process described above, as well as an enlarged image of the UCN6 nanocrystals. In FIG. 16, the scale bars are 100 nm. The TEM samples were prepared by placing a drop of UCNs in cyclohexane onto the surface of a copper grid. Overall, the nanocrystals produced were rod-shaped with an average size of 250-450 nm in length and 40-60 nm in width.

Figure 17:
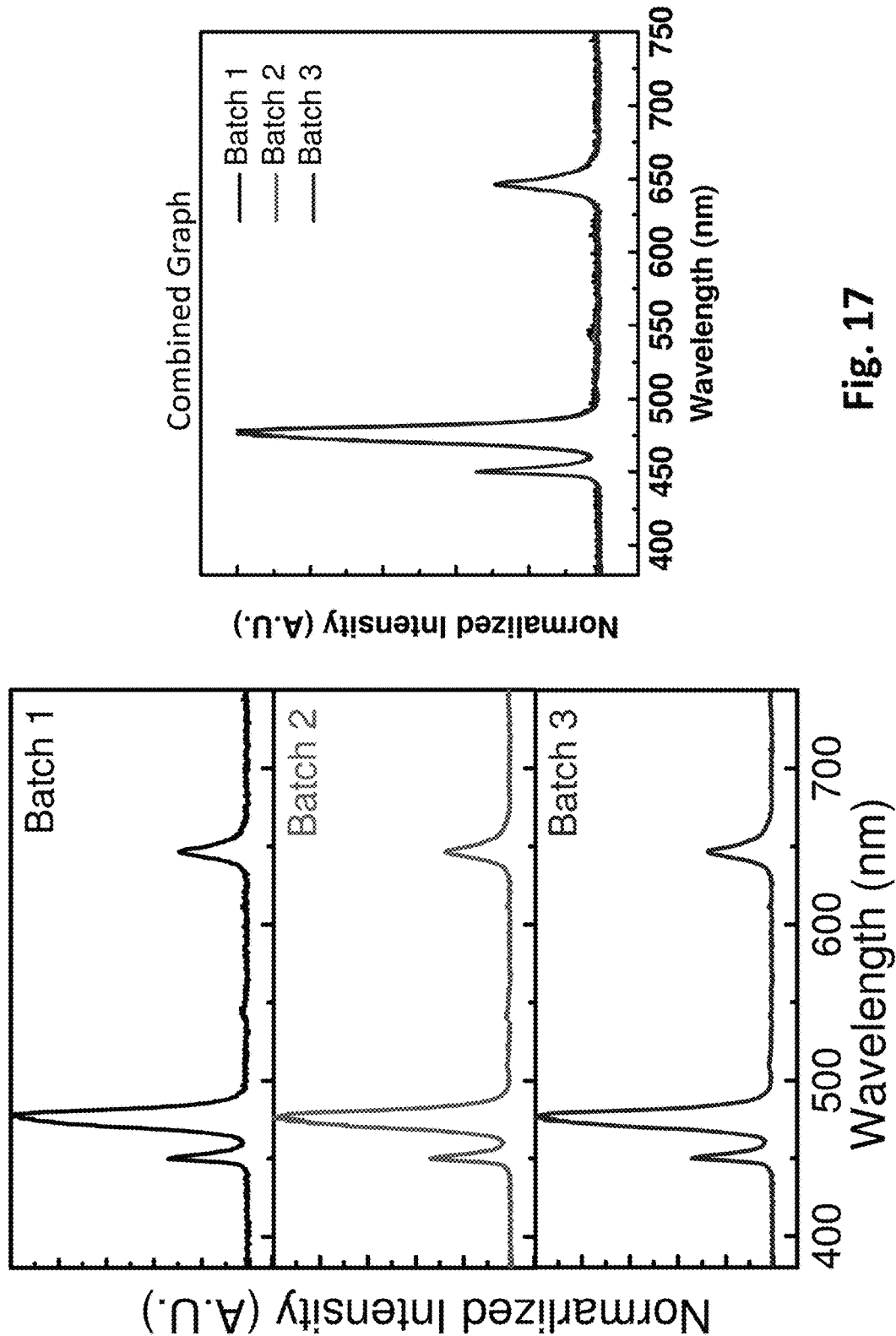
FIG. 17 includes graphs of emission spectra for different batches of UCNs, in accordance with some embodiments.

The inventors made several different batches of the same type of nanocrystals to confirm that the emission spectra were consistent from batch to batch. Upconversion luminescence spectra of UCNs were measured in a poly (urethane acrylate) (PUA) prepolymer solution (9/1 PUA/PI (v/v)) with a fluorescence spectrometer with a 1 W CW diode laser (980 nm) used as the excitation source. FIG. 17 shows the normalized emission spectra for three different batches of UCN7 type nanocrystals. As shown, emission spectra for the three different batches are practically indistinguishable on the combined graph.

Figure 18:
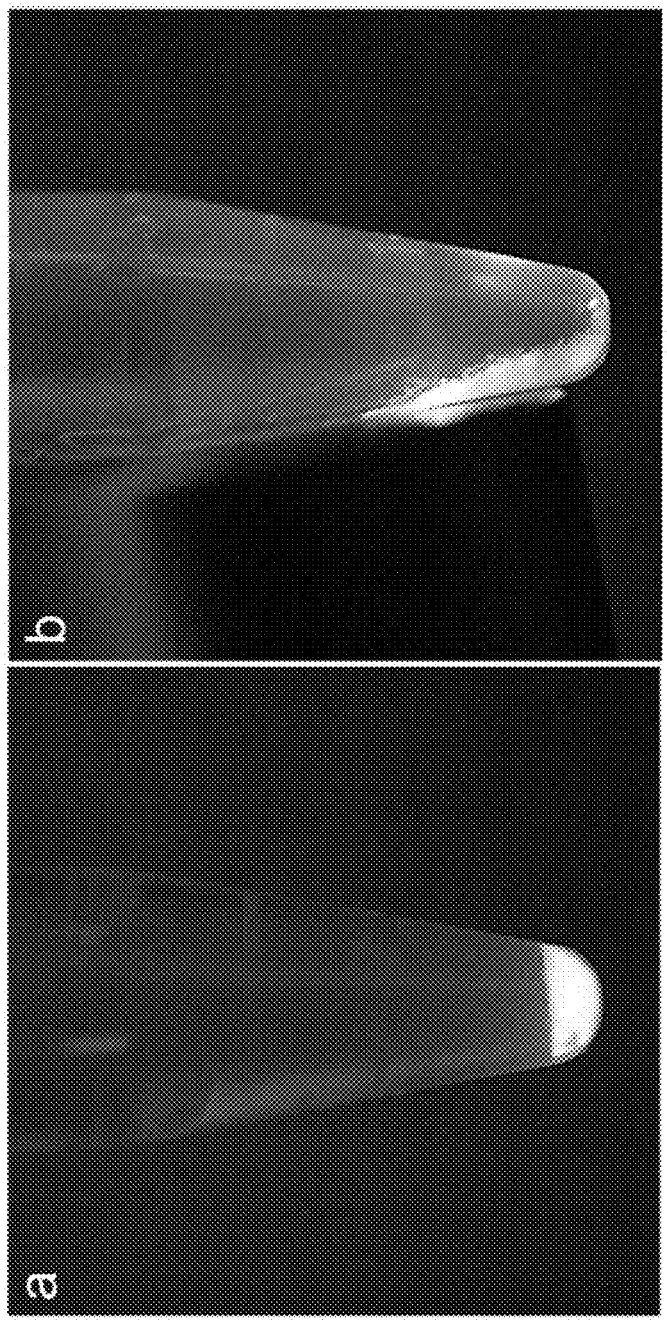
FIG. 18 includes luminescence images of UCNs in liquid with and without an applied external magnetic field, in accordance with some embodiments.
Figure 19:
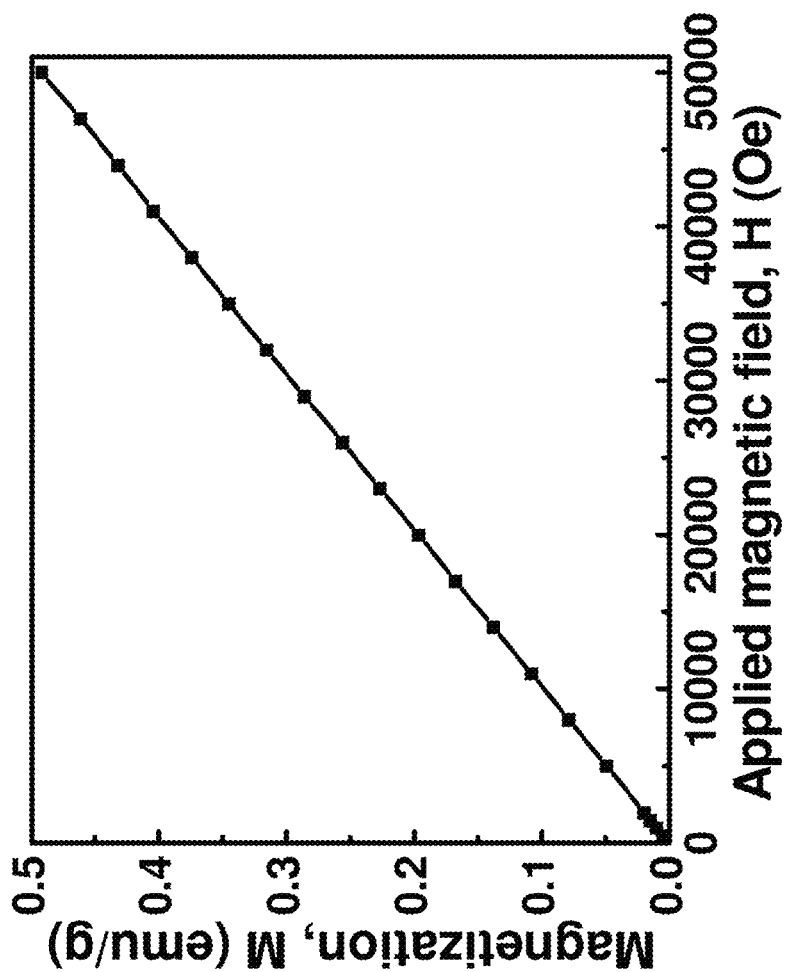
FIG. 19 is a graph of magnetization versus applied magnetic field for UCN4, in accordance with an embodiment.

The high Gd content of UCN1-UCN10 makes the UCNs paramagnetic and subject to physical manipulation through external magnetic fields. The inventors confirmed this by manipulating the nanocrystals suspended in vials using external ferromagnets. FIG. 18 includes luminescence images of UCNs in liquid in a vial (a) settled to the bottom of the vial with no applied magnetic field, and (b) with an applied magnetic field from a ferromagnet drawing the UCNs to the left side of the vial. FIG. 19 is a graph of data for magnetization as a function of applied magnetic field for UCN4, which was obtained using a superconducting quantum interference device (SQUID).

Example Surface Modifications of UCNs

The synthesis process described above produced nanocrystals capped with oleic acid, a fatty acid with a 17-carbon hydrocarbon tail. As a result of the oleic acid capping, the resulting nanocrystals were insoluble in aqueous media, which created problems with dispersing the nanocrystals in aqueous or hydrophilic source materials. Furthermore, the nanocrystals with oleic acid tails luminesced brightly only in hydrophobic media. Exposure of the oleic acid capped UCNs to water caused significant aggregation and a high degree of reversible luminescence attenuation due to surface defect-mediated quenching.

The inventors utilized a method of modifying the oleic acid tail on the UCNs to improve their solubility in water and increase their luminescence in hydrophilic media. The oleic acid double bond was oxidized to form an alcohol, and then cleaved, thereby releasing the outward-facing hydrophobic part of the oleic acid chain and forming a carboxylic acid group.

The specific procedure employed to modify the oleic acid tail of the UCNs involved adding 0.1 gram of UCNs to a mixture of cyclohexane (100 mL), tert-butanol (70 mL), water (10 mL) and 5 wt % $K_2CO_3$ solution (5 mL) and stirring for about 20 minutes at room temperature. Then, 20 mL of Lemieux-von Rudloff reagent (5.7 mM $KMnO_4$ and 0.1 M $NaIO_4$ aqueous solution) was added dropwise to the solution. The resulting mixture was stirred for 48 hours. The product was centrifuged and washed with deionized water, acetone, and ethanol. Subsequently, the UCNs were dispersed in hydrochloric acid (50 mL) of pH 4, and stirred for 1 hour forming carboxyl-terminated nanocrystals, which were washed 5 times with deionized water and collected by centrifugation. The resulting carboxyl-terminated nanocrystals dispersed without aggregation in aqueous media and luminesced strongly in hydrophilic media. The surface modification is useful if hydrophilic materials are being used for the microparticle body; however, it may not be needed for hydrophobic materials like PUA.

The inventors developed a method for modifying the carboxyl-terminated UCNs to form acrylate-terminated UCNs that could be cross-linked with the polymer material of the microparticle. The method included mixing 200 μl of EDC (20 mg/ml) and 200 μl of sulfo-N-hydroxysuccinimide (sulfo-NHS) (20 mg/ml) with 200 μl of carboxy-terminated UCNs in 2-(N-morpholino) ethanesufonic acid (MES) buffer (0.1 M, pH 6.0, 40 mg/ml) and stirring for two hours at room temperature to activate the surface as carboxylic acid groups. The NHS-activated UCNs were centrifuged and washed with water. The precipitate was re-dispersed 200 μl of PBS buffer (0.1 M, 5 ml, pH 7.2) containing 2-hydroxyethylacrylate (20 mg/ml). The mixture was then stirred for 24 hours at room temperature. The resulting acrylated UCNs were purified by repeated centrifugation (3000 rpm, 5 min, 5 times) and re-suspended in deionized water.

Figure 20:
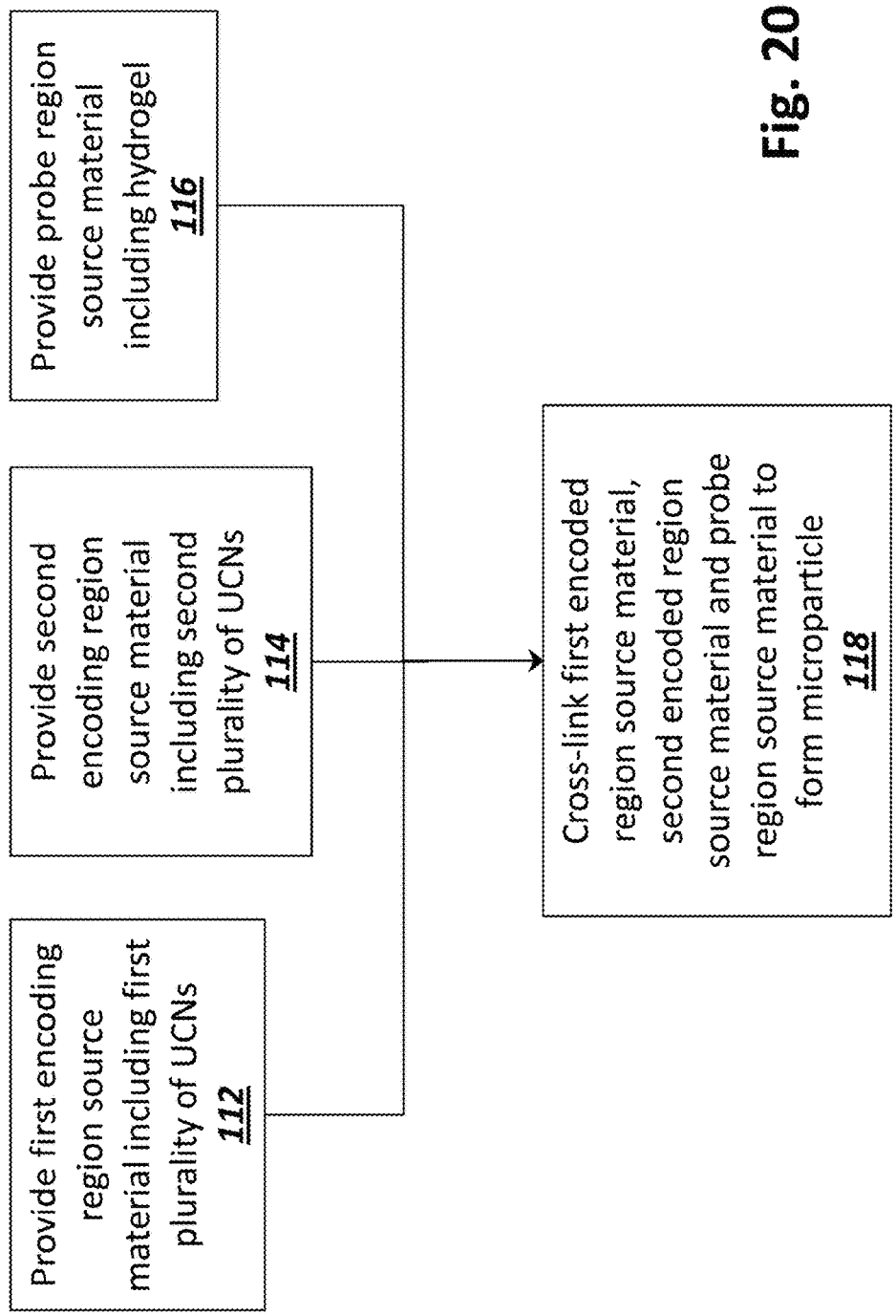
FIG. 20 is a block diagram schematically representing a method of forming a contiguous microparticle, in accordance with an embodiment.

FIG. 20 is a flow diagram 110 of a method of making a polymer microparticle for labeling an object or tissue. A first encoded region source material is provided (112). The first encoded region source material includes a polymer and a first plurality of UCNs having a first spectral signature. For example, the first plurality of UCNs may be the nanocrystals described above and labeled UCN3. The spectral signature of the first plurality of the UCNs (type UCN3) may be described as the spectrum shown in FIG. 4, or may be described by the ratio of the integrated intensity in one detection channel relative to another detection channel (e.g., the ratio of the green detection channel integrated intensity the red detection channel integrated intensity as shown in Table 1), or by multiple different integrated intensity ratios (e.g., green to red, blue to red, red to green). A second encoded region source material is also provided (114). The second encoded region source material includes a second plurality of UCNs having a second spectral signature different than the first spectral signature. The second plurality of UCNs may be the UCNs described above and labeled UCN4. In some embodiments, a probe region source material including a hydrogel material is also provided (116). The spectral signature of the second plurality of the UCNs (type UCN4) may be described as the spectrum shown in FIG. 5, or may be described by the ratio of the integrated intensity in one detection channel relative to another detection channel (e.g., the ratio of the green detection channel integrated intensity the red detection channel integrated intensity as shown in Table 1), or by multiple different integrated intensity ratios (e.g., green to red, blue to red, red to green). Although the flow chart only specifies a first encoded region source material and a second encoded region source material, the number of encoded region source materials required corresponds to the number of portions of the encoded region desired in the resulting microparticle.

The first encoded region source material the second encoded region source material and the probe region source material are cross-linked forming the first portion of an encoded region 31, and the second portion of the encoded region 32, and the probe region (118). The probe region is cross-linked with one or both of the first portion 31 and the second portion 32 of the encoding region to form a contiguous microparticle. In embodiments with more than two portions of the encoded region, each portion is cross-linked with one or more other portions of the encoded region forming the contiguous microparticle.

In some embodiments, the UCNs for at least some of the portions of the encoded region have a hydrophilic surface. In some embodiments, the UCNs for at least some of the portions of the encoded region have a hydrophilic ligand. In some embodiments, providing the first encoded region source material and providing the second encoded region source material may include modifying the first plurality of nanocrystals and the second plurality of nanocrystals to have a hydrophilic surface and/or a hydrophilic ligand. Having a hydrophilic surface and/or a hydrophilic ligand may aid in dispersing the UCNs in an aqueous or hydrophilic source material. For example, in some tissue labeling applications, a hydrogel material may be used for the body.

In some embodiments, the UCNs for at least some of the portions of the encoded region have acrylated ligands for cross-linking with the polymers of the hydrogel matrix. In some embodiments, providing the first encoded region source material and providing the second encoded region source material may include modifying the first plurality of nanocrystals and the second plurality of nanocrystals to include acrylated ligands. In some embodiments, the plurality of UCNs is bound to the polymer material at the time of particle synthesis through an acrylate group.

In other embodiments, another type of covalent linkage could be made between the UCNs and the polymer matrix. The UCNs can be bound to the polymer matrix using any number of covalent attachment mechanisms (e.g., amide linkages, disulfides, esters, ethers, aldehydes/ketones, cycloadditions, click chemistry, azides, and carbamates).

In some embodiments, the body includes a hydrophobic polymer material such as PUA. In these embodiment, the nanocrystals employed may have a hydrophobic surface or a hydrophobic ligand. Oleic acid-capped nanocrystals need not be modified to disperse in a hydrophobic material such as PUA.

In some embodiments, at least some of the UCNs are doped with rare-earth metals. In some embodiments, at least some of the UCNs are doped with a composition including at least 30 mol % Gd. In some embodiments, at least some of the UCNs are paramagnetic.

In some embodiments, the material for each portion of the encoded region is the same material. In some embodiments, the material for some portions of the encoded region is different than the material for the other portions of the encoded region.

As noted above, in some embodiments the UCNs have a hydrophilic surface. In some embodiments, the UCNs have a hydrophilic ligand. Having a hydrophilic surface and/or a hydrophilic ligand may aid in dispersing the UCNs in the source material.

In some embodiments, the method also includes co-flowing the source material for each encoded region to an area for cross-linking. For example, a stop-flow lithography (SFL) technique may be employed for forming the microparticles. In SFL, viscous UV-sensitive pre-polymer solutions (which may be referred to herein as source materials) undergo laminar co-flow into a small microfluidic device, which may be made of polydimethylsiloxane (PDMS). For organic synthesis, the microfluidic device may be made from perfluoropolyether (PFPE). The flow of the pre-polymer solutions is stopped for a brief period in which the pre-polymer solutions in the device are exposed to photomask-patterned ultraviolet light. The UV light causes cross-linking, polymerization, or both within milliseconds in the region delineated by the photomask forming micro-sized polymeric particles. The shape of each particle is defined by the photomask. The composition of each striped portion of the particle is determined by the composition of the laminar co-flowing streams (e.g., the source materials). The SFL technique is particularly well suited for spatial and spectral encoding of microparticles using nanocrystals because of the ability to control both overall microparticle particle shape and the composition of different striped portions of the microparticle.

Figure 21:
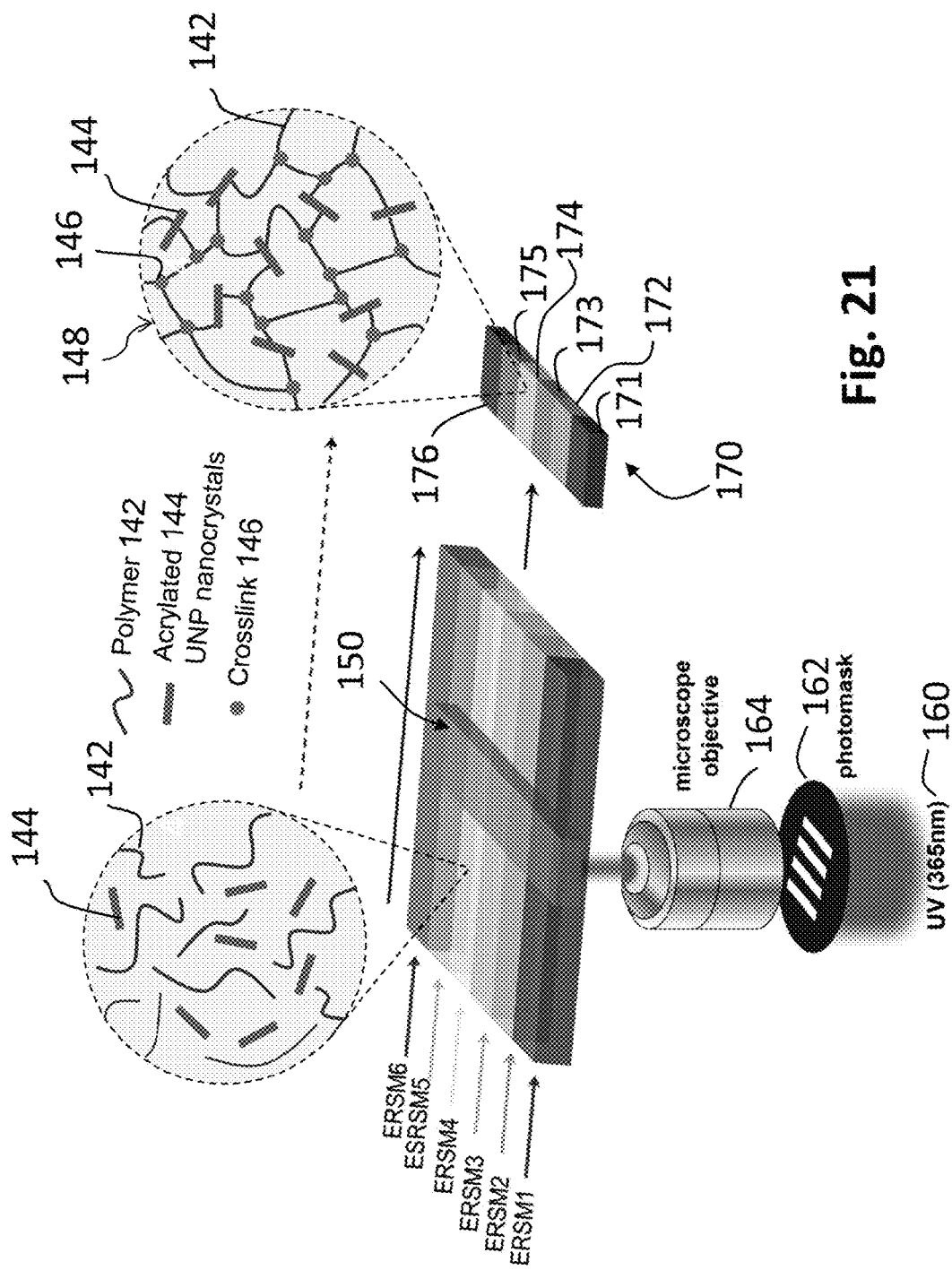
FIG. 21 schematically depicts a stop flow lithographic method of forming a contiguous microparticle, in accordance with an embodiment.

FIG. 21 schematically depicts SFL being used to make a hydrogel microparticle with an encoding region including different portions having UCNs with distinguishable spectral signatures. In the diagram the encoded region source materials (ERSMs) are labeled ERSM1-ESRM6. Each of the encoded region source materials includes a pre-polymer 142 and a plurality of UCNs, which may be acrylated UCNs 144 in some embodiments. As used herein, the term pre-polymer includes monomers, and polymer chains that can be cross-linked. As used herein, the term cross-linking refers broadly to forming links between polymer chains, to forming links between a polymer and a nanoparticle, and to polymerization of monomers. The one or more encoded region source materials ERSM1-ERSM6 are flowed to an area 150 within a microfluidic device. When the co-flows are briefly stopped, a light source 160 (e.g., a 350 nm UV light source) a photomask 162 and a focusing optic (e.g., objective lens 164) provide patterned and focused light at the area 150 for cross-linking/polymerization of the pre-polymer 142. Cross-linking 146 of the pre-polymer source materials forms the contiguous microparticle 170 by creating a polymer network. As shown, the UCNs 144 may include acrylated ligands, which allows the UCNs 144 to crosslink 146 with the polymer network 148. Each encoded region source material ERSM1-ERSM6 forms a corresponding portion 171-176 of the encoded region of the microparticle 170. In some embodiments, the UCNs are not cross-linked with the polymer network, but instead are physically entrained by the matrix pore size of the polymer network 148.

Although photomask 162 is shown having a pattern that forms four microparticles simultaneously, in some embodiments, the photomask may have a pattern for forming more than four microparticles simultaneously. In some embodiments, only one microparticle may be formed at a time. In some embodiments, a photomask may have a pattern that produces microparticles having different shapes simultaneously. In some embodiments, the photomask may produce asymmetric particles and/or particles having nonrectangular shapes.

Figure 22:
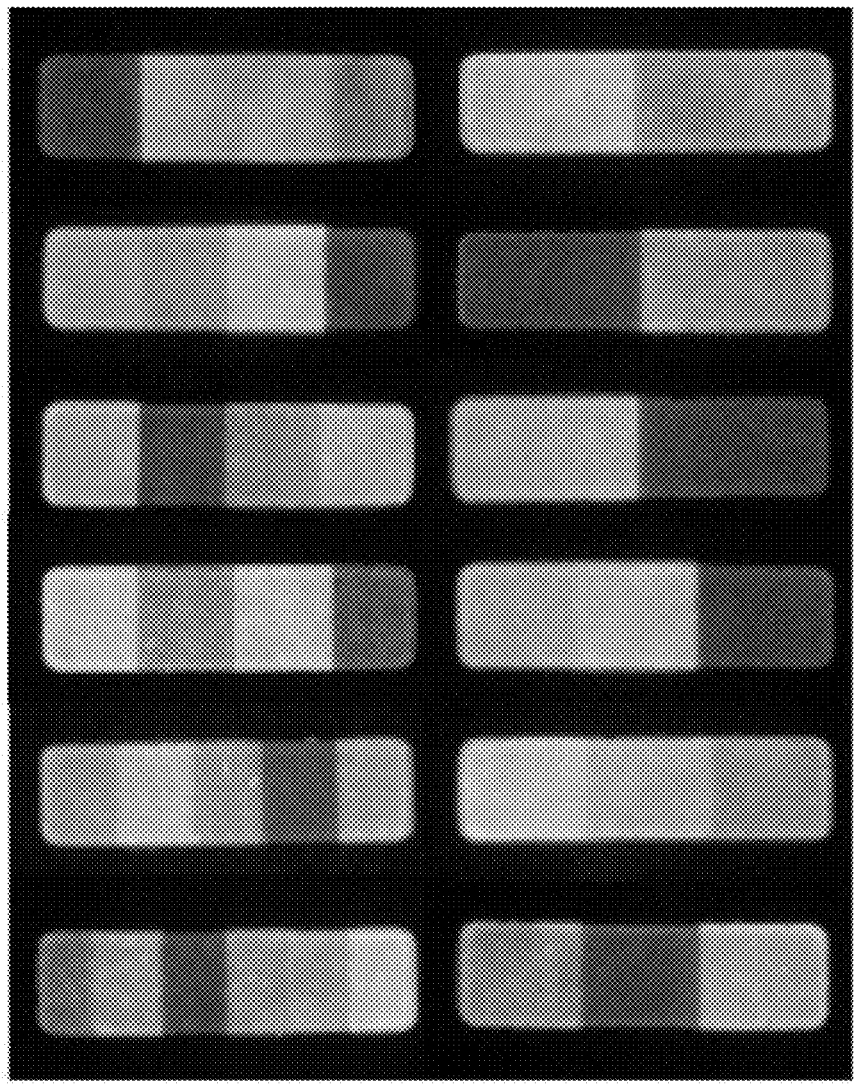
FIG. 22 is a luminescence image of microparticles having different numbers of encoded regions, in accordance with some embodiments.

Although microparticle 170 is shown with six encoded regions, in other embodiments, there may be more or fewer than six encoded regions. For example, FIG. 22 shows luminescence images of various microparticles each having between two to six encoded regions. Microparticles with an additional encoding region (e.g., seven stripes instead of six) would boost single particle encoding capacities to over 10 million, while requiring little more than an additional input port on the microfluidic synthesis device.

Figure 44:
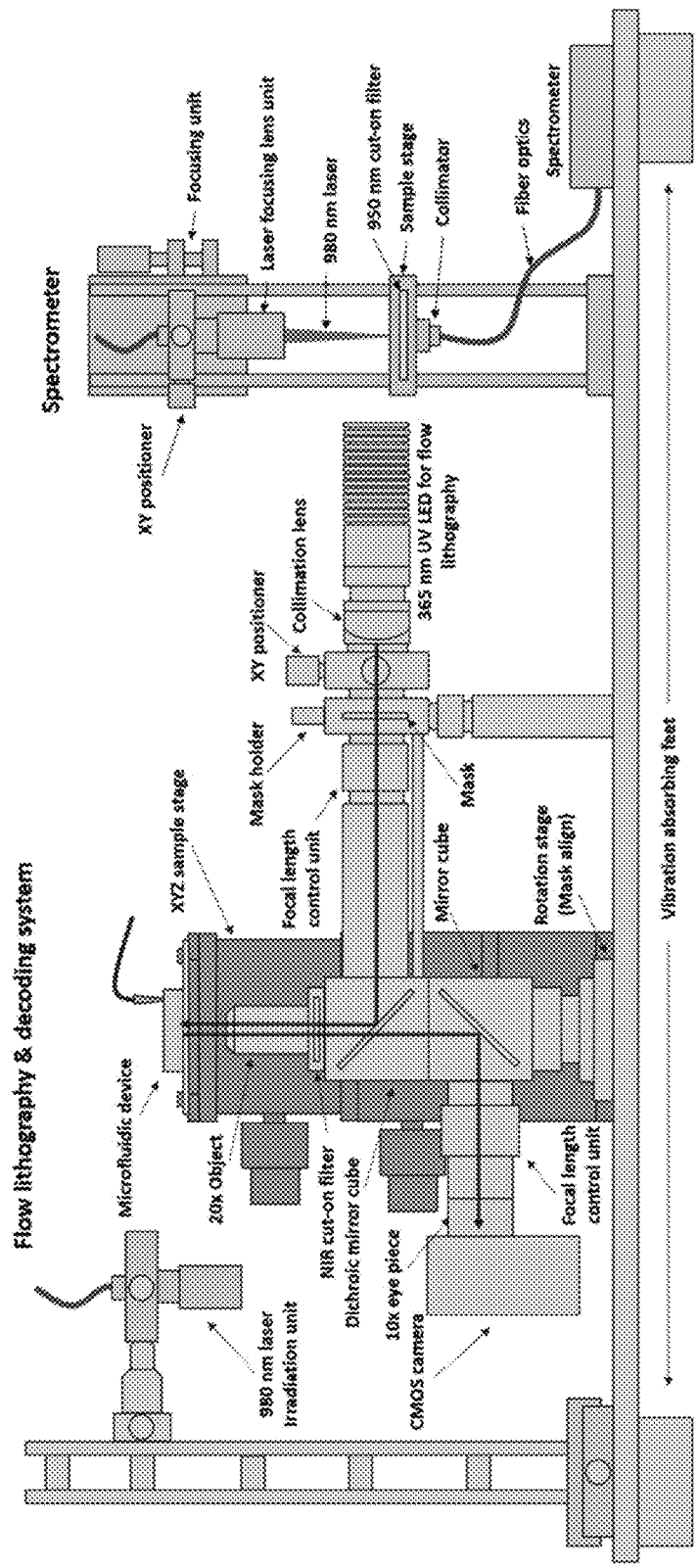
FIG. 44 schematically depicts a flow lithography and decoding system for particle synthesis, in accordance with some embodiments.
Figure 45:
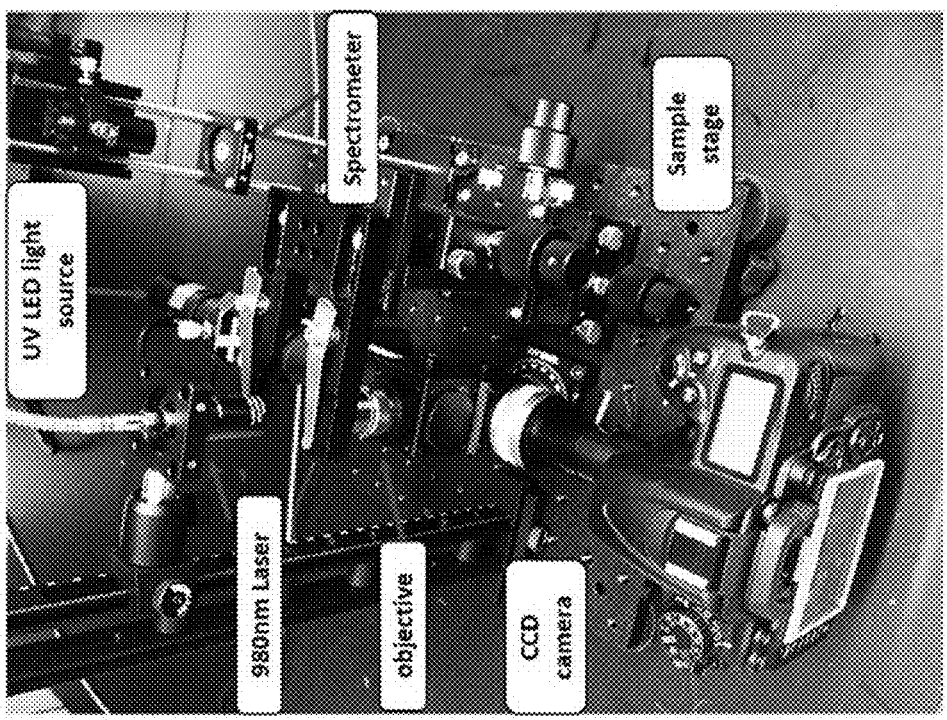
FIG. 45 is an image of the system for particle synthesis of FIG. 44.

For further details regarding the SFL technique for forming contiguous polymer microparticles, see U.S. Patent Application Publication No. US 2012/0316082 A1, published Dec. 13, 2012, and U.S. Patent Application Publication No. US 2012/0003755 A1, published Jan. 5, 2012, each of which is incorporated by reference herein in its entirety An exemplary flow lithography system is described below with respect to FIGS. 44 and 45

Example Production of PEG-DA Hydrogel Microparticles with UCNs

Figure 23:
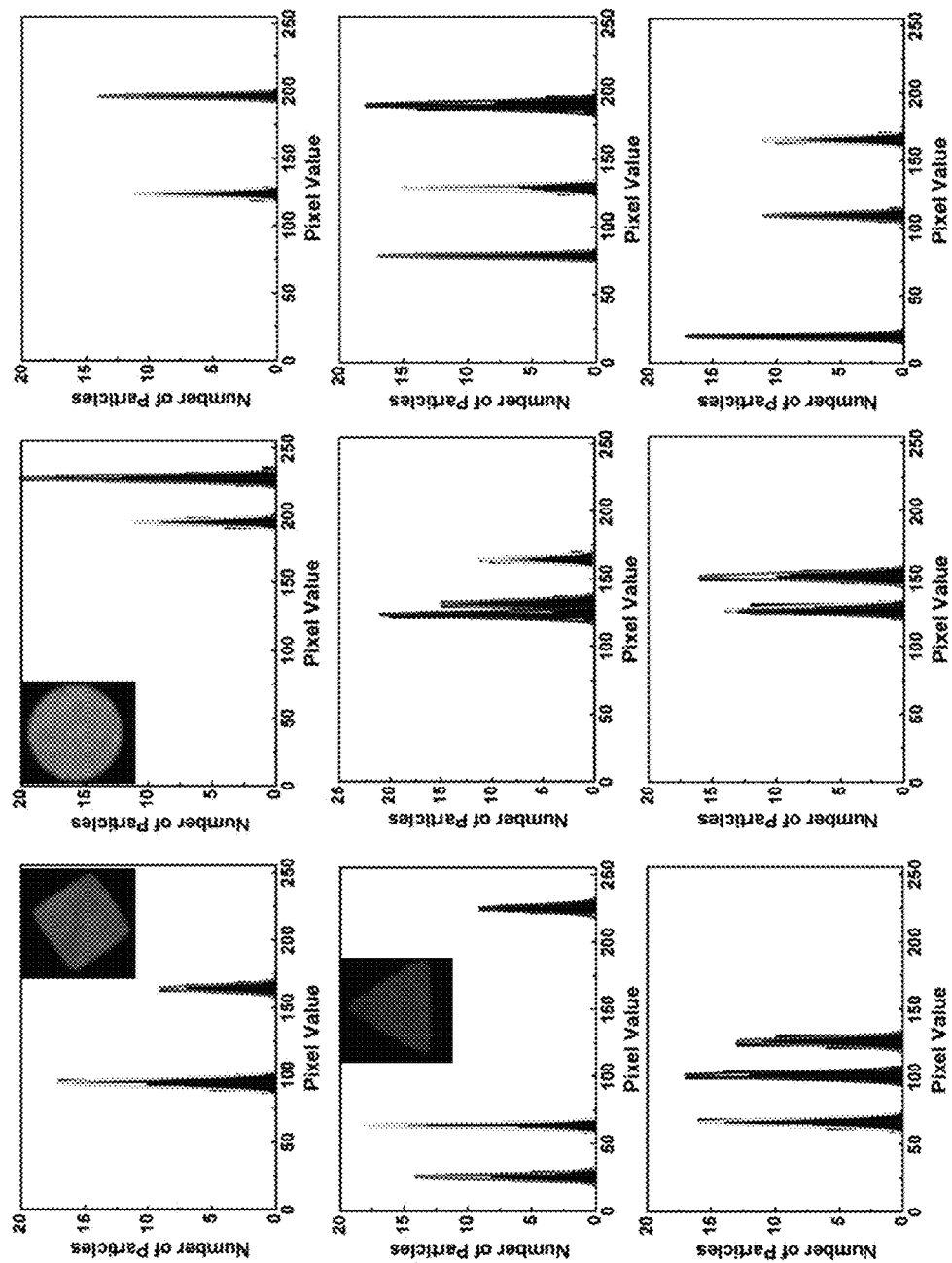
FIG. 23 includes graphs of integrated intensity values for microparticles, each including a different type of UCNs, in accordance with some embodiments.

The inventors produced polyethylene glycol diacrylate (PEG-DA) polymer microparticles by stop flow lithography. Initially, the inventors made sets of microparticles, with each set including only one type of nanocrystal to determine whether incorporating the nanocrystals into microparticles changes the emission spectral of the nanocrystals. For each of the nanocrystal types UCN1-UCN10, fifty PEG-DA hydrogel microparticles were produced. A CCD device was used to obtain a three color image (red channel, green channel and blue channel) of each microparticle while illuminated by NIR light producing a red channel image, a green channel image and a blue channel image. For each channel image, the intensity (pixel value) within the boundaries of each microparticle was integrated yielding a "pixel value" for each channel for each microparticle. FIG. 23 includes histograms of the integrated "pixel values" for the red, green and blue channels from fifty microparticles for the UCN1-UCN9 types. The histograms for some of the types also include an inset image of a representative NIR-illuminated microparticle. As shown by the inset images, a stop flow lithography process can be used to make different microparticle shapes.

The mean measured integrated intensity values from fifty microparticles for each type of UCNs were then compared with the expected integrated intensity data obtained from a convolution of the UCN emission data and the image sensor response curves. Table 3 below includes measured mean integrated intensity data, the standard deviation and the coefficient of variability for UCNs in microparticles. Expected integrated intensity data based on emission spectra from UCNs in solution are also included for comparison. As shown in the table, the mean integrated intensity and the expected integrated intensity values are consistent. The average coefficient of variation across all particles and UCN colors was 2%. This corresponds to an average standard deviation of 2.1 RGB units (on a scale of 255) for separately acquired images of separately synthesized particles, indicating outstanding particle-to-particle reproducibility. In addition, error ellipses are non-overlapping to better than 6 sigma, indicating that decoding error rates of less than 1 ppb are to be expected. Thus, if the emission spectrum of a type of nanocrystals is known, the integrated intensity for detection in a color channel can be reliably predicted.

TABLE 3

| Type Channel | Expected Integrated Intensity R | Mean Integrated Intensity ± standard deviation R | Cv R | Expected Integrated Intensity G | Mean Integrated Intensity G | Cv G | Expected Integrated Intensity ± standard deviation B | Mean Integrated Intensity ± standard deviation B | Cv |
|---|---|---|---|---|---|---|---|---|---|
| UCN1 | 130.3 | 126.34 ± 1.43 | 0.02 | 68.5 | 65.30 ± 2.29 | 0.03 | 103.7 | 100.74 ± 2.48 | 0.02 |
| UCN2 | 103.3 | 109.10 ± 1.87 | 0.01 | 44.8 | 42.70 ± 1.39 | 0.03 | 10.2 | 17.37 ± 1.43 | 0.08 |
| UCN3 | 164.5 | 164.29 ± 2.26 | 0.01 | 91.9 | 91.73 ± 2.73 | 0.02 | 0 | 0 | — |
| UCN10 | 161.6 | 160.86 ± 1.3 | | 131.5 | 130.97 ± 1.3 | | 0 | 0 | — |
| UCN4 | 225.4 | 225.89 ± 2.29 | 0.01 | 197.5 | 194.71 ± 2.01 | 0.01 | 0 | 0 | — |
| UCN5 | 91.9 | 86.10 ± 1.42 | 0.01 | 164.5 | 161.77 ± 1.89 | 0.01 | 0 | 0 | — |
| UCN6 | 120.4 | 123.52 ± 2.15 | 0.01 | 158.1 | 163.40 ± 2.04 | 0.01 | 138.5 | 132.29 ± 2.54 | 0.02 |
| UCN7 | 24.7 | 23.54 ± 2.02 | 0.08 | 55.1 | 63.22 ± 1.93 | 0.03 | 219.9 | 222.36 ± 2.9 | 0.01 |
| UCN8 | 83.2 | 78.37 ± 2.59 | 0.01 | 132.6 | 128.58 ± 2.63 | 0.02 | 182.2 | 189.61 ± 1.89 | 0.01 |
| UCN9 | 158.9 | 151.34 ± 2.02 | 0.01 | 131.1 | 127.62 ± 1.93 | 0.02 | 120.6 | 125.73 ± 2.92 | 0.02 |

Figure 24:
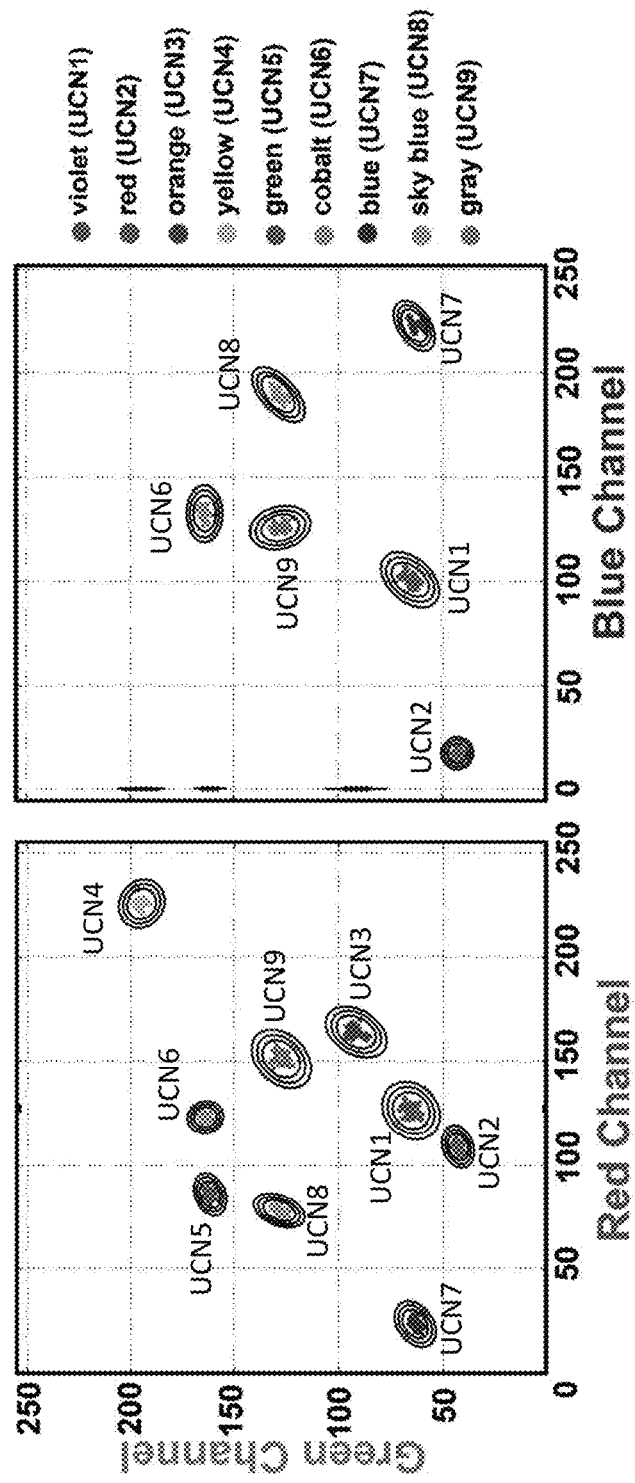
FIG. 24 is a scatter plot of integrated intensity data for microparticles including different types of nanocrystals, in accordance with some embodiments.
Figure 25:
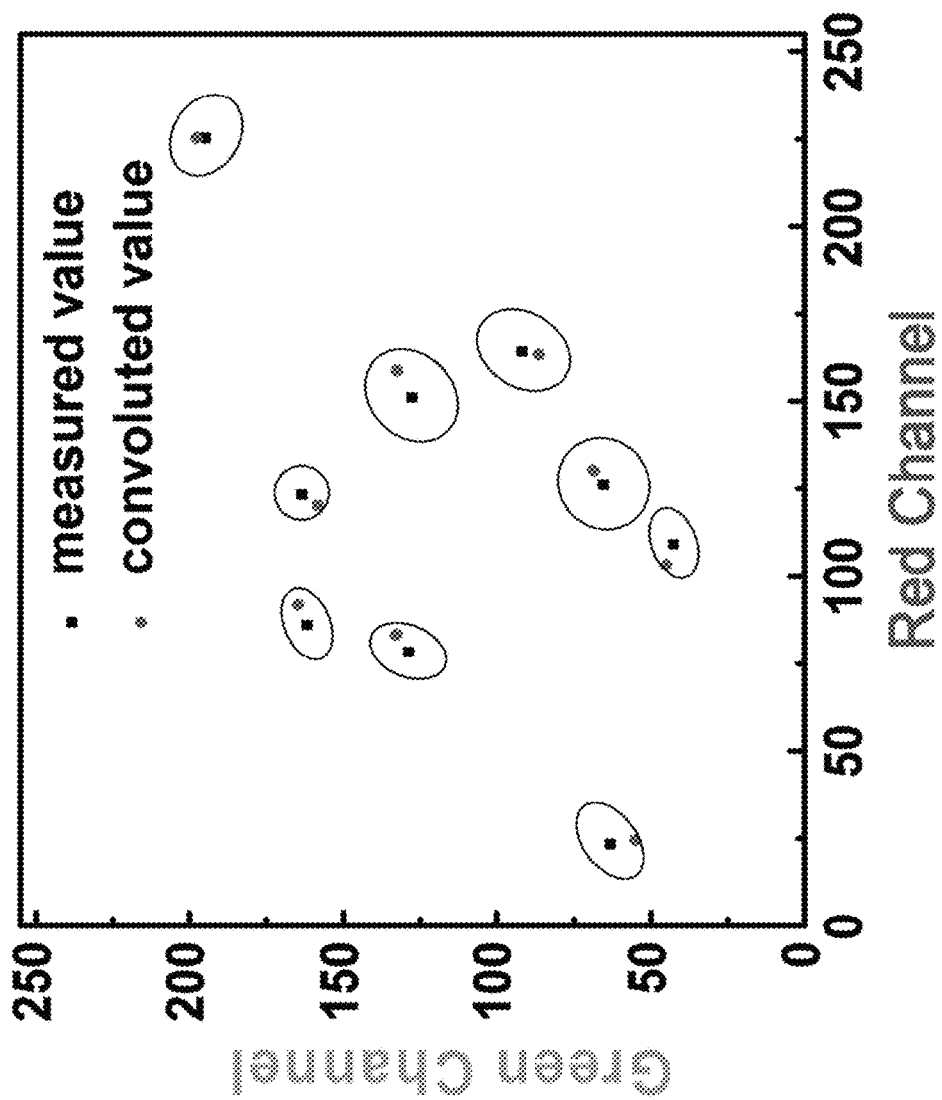
FIG. 25 is a plot of mean measured integrated intensity data and expected integrated intensity date for the red channel versus the green channel showing five-sigma confidence contours, in accordance with an embodiment.

FIG. 24 is a scatterplot showing the red channel, green channel, and blue channel integrated intensity values for each microparticles incorporating the UCN1-UCN9 type nanocrystals. All of the UCN1-UCN9 types of nanocrystals have red channel and green channel emission intensities. The UCN1, UCN2, UCN6, UCN7, UCN8 and UCN9 types of nanocrystals have emission intensities in the blue channel as well as the red and green channels. The ellipses around each cluster of data points are the three-sigma, four-sigma and five-sigma contours derived from fitting a Gaussian mixture model to the data. As shown by separation between the tight clusters, the UCN type for each microparticle can clearly be distinguished using the red channel, green channel, and blue channel integrated intensities for the microparticle. FIG. 25 shows a comparison of the mean integrated intensity value (measured value squares) and the expected integrated intensity value (convoluted value circles) in the green channel versus the red channel for particles integrating UCN1-UCN9 types of nanocrystals. The ellipses represent the five-sigma confidence contours.

Thus, the inventors demonstrated noise-robust spectral discrimination of six different types of UCNs integrated in polymer particles illuminated using an NIR diode laser and imaged using a standard CCD camera. Further, as shown by the green channel vs. red channel plot, the red channel integrated intensity and the green channel integrated intensity are sufficient to distinguish between the six different types of nanocrystals. The FIGS. 24 and 25 scatter plots reveal that cluster overlap occurs only past six standard deviations from the mean, implying an expected error rate of less than 1 part per billion (ppb).

Figure 26:
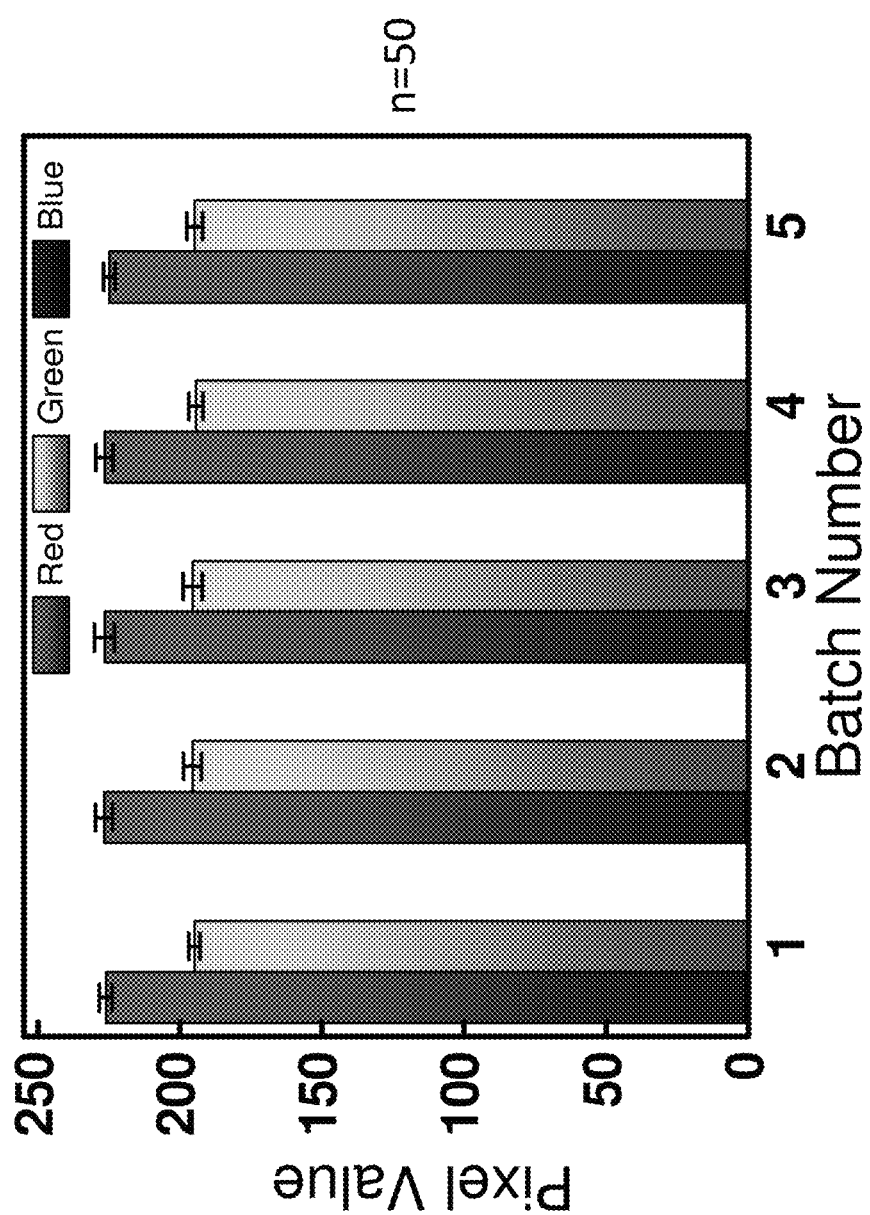
FIG. 26 shows integrated intensity data for different batches of microparticles, in accordance with some embodiments.

The inventors also compared different batches of microparticles produced at different times to determine the reliability and the predictability of the integrated intensities of microparticles from different batches. Five separate batches of fifty microparticles were produced, each batch including the same UCN4 type nanocrystals. The microparticles were illuminated with an NIR light source and color images were obtained using a CCD camera. Integrated intensity data was generated for microparticles in all five batches and the average integrated intensity values for each batch were compared. FIG. 26 is a graph comparing the average integrated intensities for the green channel and for the red channel for each batch of fifty microparticles. The integrated intensities in the red and green channels were consistent across the five batches. As expected, there was no detected signal the blue channel. Table 4 below lists the measured red and green channel integrated intensity values for each batch showing the consistency and reproducibility of the spectral signature for different batches of microparticles.

TABLE 4

| Type | Red Channel Mean Integrated Intensity ± standard deviation | Green Channel Mean Integrated Intensity ± standard deviation |
|---|---|---|
| 1 | 225.89 ± 2.29 | 194.71 ± 2.01 |
| 2 | 226.51 ± 2.97 | 195.46 ± 3.14 |
| 3 | 226.35 ± 3.42 | 195.36 ± 3.34 |
| 4 | 226.36 ± 3.01 | 194.22 ± 2.46 |
| 5 | 224.65 ± 2.05 | 194.68 ± 2.77 |

Figure 27:
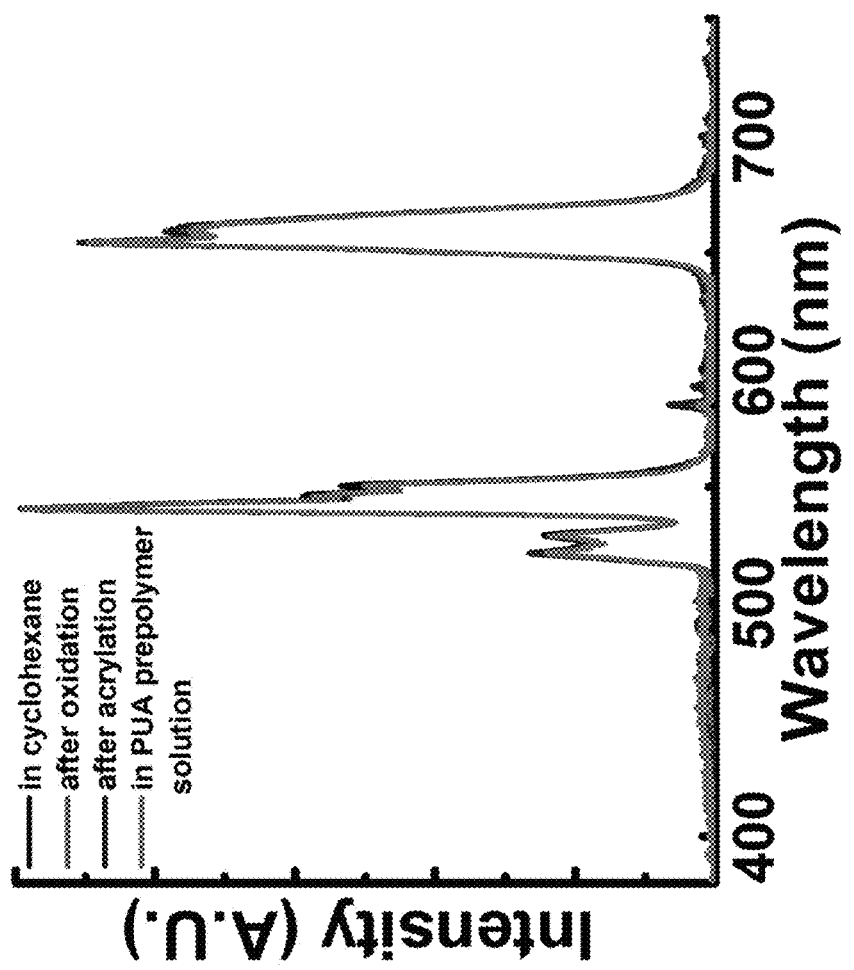
FIG. 27 is a graph of emission spectra of UCN 4 after each step in surface chemical modification of the UCNs, in accordance with some embodiments.

The inventors confirmed that the oxidation and acrylation process does not change an emission spectrum of the UCNs. FIG. 27 is a graph of emission spectra of UCN4 type nanocrystals after each step in the surface chemical modification of the UCNs (e.g., before processing in cyclohexane, after oxidation, after acrylation, and in PUA prepolymer solution). The spectra overlay each other establishing that surface chemistry modifications of the UCNs before incorporation into microparticles does not significantly affect emission spectra of the resulting particles.

Figure 28:
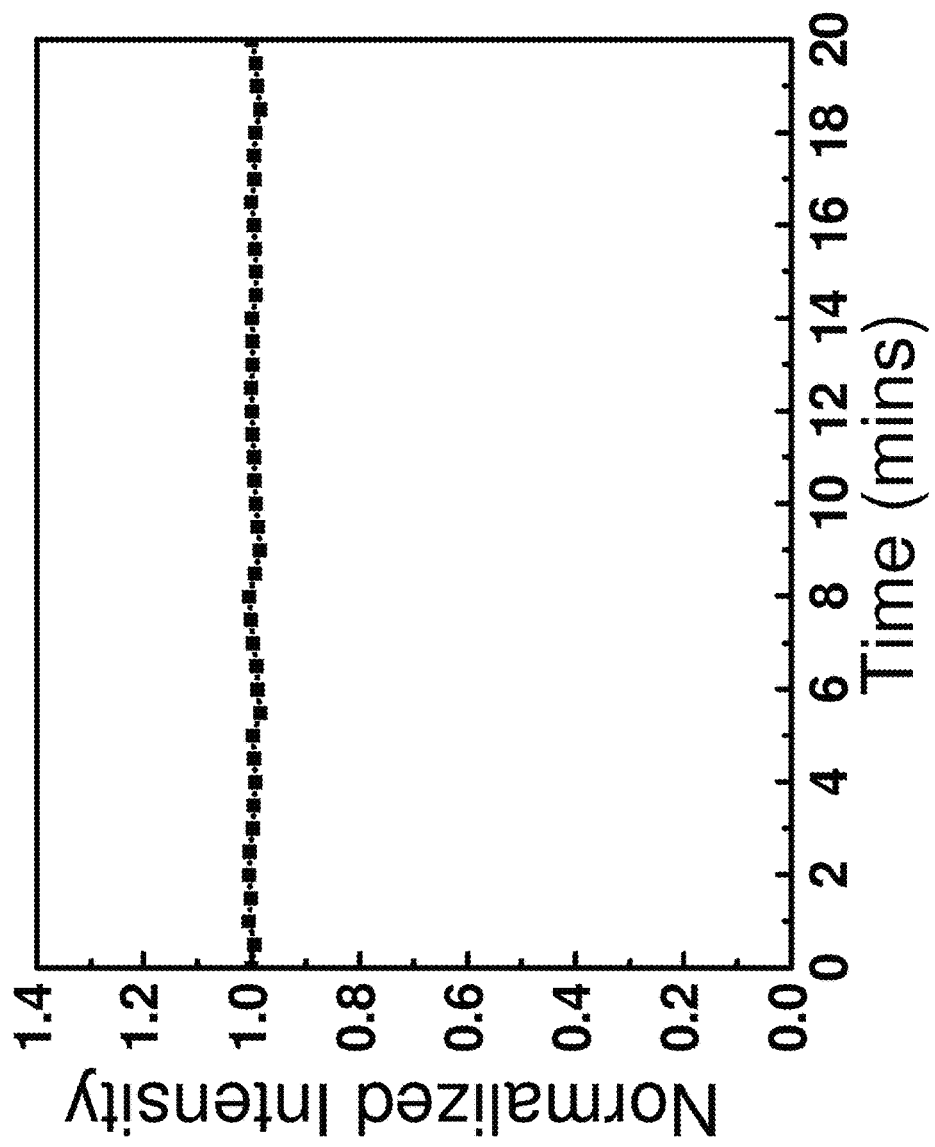
FIG. 28 shows microparticle emission intensity as a function of time during intense sustained NIR irradiation, in accordance with some embodiments.

The inventors also confirmed that there was no attenuation of the luminescence response of the nanocrystals integrated into hydrogel microparticles upon prolonged intense NIR irradiation due to photobleaching. FIG. 28 is a graph of intensity as a function of time for hydrogel microparticles including UCN7 type nanocrystals upon continuous exposure to a 980 nm NIR light from a 1 W laser. This is in contrast to many commonly used fluorophores which exhibit attenuation due to photobleaching.

Figure 29:
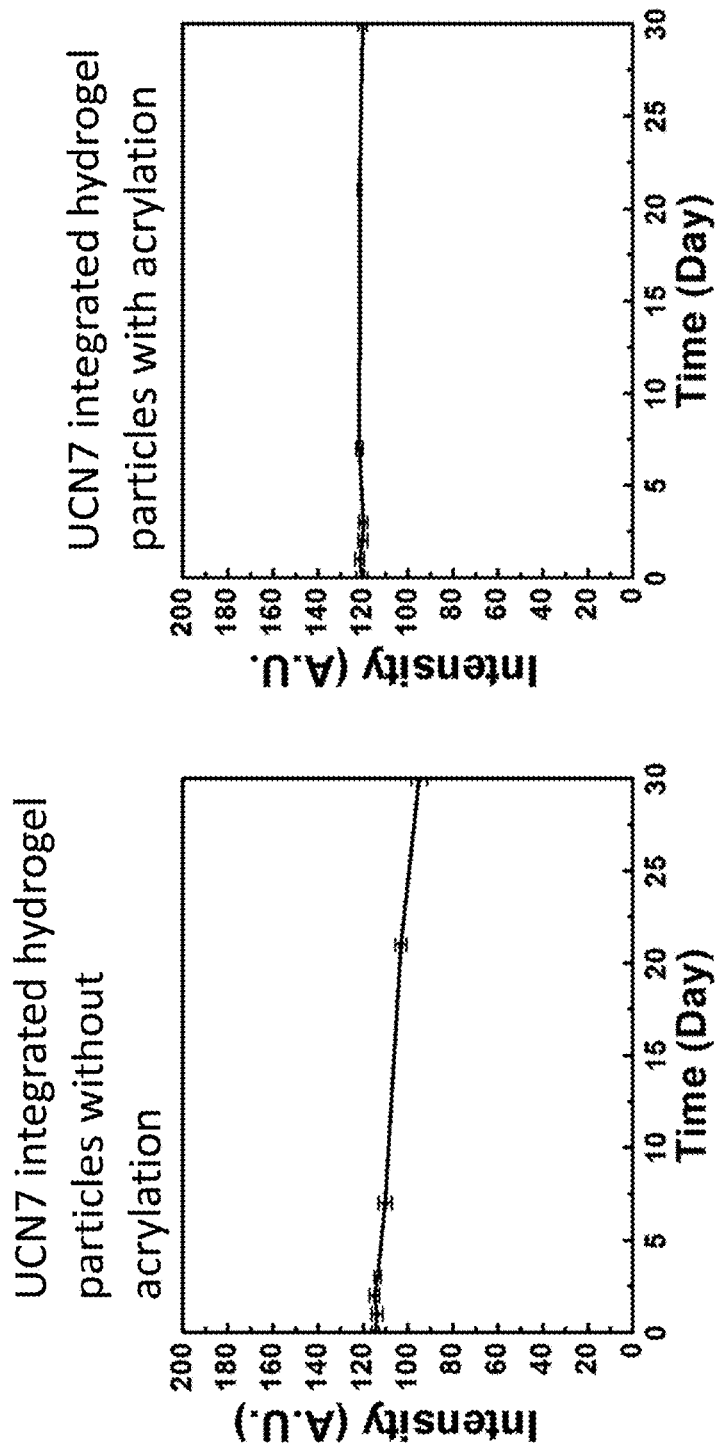
FIG. 29 shows graphs of intensity versus microparticle age for microparticles with carboxyl-terminated UCN and for microparticles with acrylated UCN, in accordance with some embodiments.

The inventors also compared the stability of hydrogel microparticles made with carboxyl-terminated UCNs, in which the nanocrystals are trapped in pores in the hydrogel matrix, and hydrogel particles made with acrylated UCNs, in which the nanocrystals are bonded to the hydrogel matrix via acrylates. FIG. 29 includes graphs comparing intensity as a function of age of microparticles including acrylated UCN7 type nanocrystals and microparticles including carboxyl-terminated UCN7 type nanocrystals without acrylation. As shown, there is a reduction in emission intensity of the microparticles including carboxyl-terminated UCNs without acrylation over 30 days, presumably due to the UCNs diffusing out of the microparticles. In contrast, the microparticles with acrylated UCNs showed no attenuation over 30 days of aging. Thus, acrylation of the UCNs and subsequent bonding to the hydrogel matrix improves the luminescence stability (e.g., the shelf-life) of the microparticles.

Example Formation of Contiguous Microparticles with Spectral and Spatial Encoding After establishing the predictability and reproducibility of the method for forming UCNs and the predictability and reproducibility of the spectra from hydrogel particles that each include only one type of UCNs, the inventors produced PEG-DA hydrogel microparticles and polyurethane acrylate (PUA) microparticles with both spectral and spatial encoding. The PUA microparticles are thermally and chemically resistant The PEG-DA microparticles are biocompatible and mesoporous allowing diffusion of large biological macromolecules. For the more densely cross-linked PUA particles, hydrophobic UCN surface chemistry and large, rod-like UCN nanostructure enabled homogeneous and irreversible physical entrainment of the UCNs in the microparticle. In contrast, stable integration of UCNs into microparticles involved use of hydrophilic surface chemistry with a UV-active functional group on the UCNs for strong, covalent incorporation as described above.

Specifically, elongated polymer microparticles were produced that each included encoding region divided into multiple portions (e.g., multiple stripes), with each portion including a plurality of nanocrystals having distinguishable spectral signature. Although the microparticles produced included two, three, four, five or six portions of an encoded region, in some embodiments, each microparticle may have an encoded region with more than six portions. In some embodiments, some particles may have different number of portions than other microparticles. Although the hydrogel microparticles produced were rectangular and elongated, in some embodiments, the hydrogel microparticles may have a different aspect ratio and/or a different shape. Further, the microparticles produced may be symmetric or asymmetric.

The microparticles were produced by SFL using encoding region source materials. For a PEG-DA hydrogel microparticle source material, acrylated UCNs were dispersed in a PEG-DA premixture solution yielding a mixture of 45 vol % PEG-DA (Mn=700), 40 vol % UCNs (0.5 mg/µl), 10 vol % poly(stylenesulfonate) PSS, and 5 vol % DAROCUR 1173 photoinitiator (PI)). For a PUA microparticle source material 150 mg of UCNs were dispersed in 300 µl of a 9:1 volume ratio PUA/PI solution. The source materials were used to form contiguous microparticles using SFL as described above with respect to FIG. 21

A microfluidic device was fabricated from poly-dimethylsiloxane (PDMS) for the SFL system. PDMS was mixed with a curing agent in a 10:1 ratio and degassed under vacuum for 30 min. Degassed PDMS was poured onto an SU-8 master mold and cured overnight at 65° C. Channels were then cut out of the mold and bonded with a glass slide coated with partially-cured PDMS in order to assure oxygen permeability. The assembled device was fully cured overnight at 65° C. The microfluidic channel in the microfluidic device of the SFL system was 300 µm wide and 36 µm high.

A photomask for the SFL was designed using a computer added drafting program and printed with a high-resolution printer. The mask was placed in the field-stop of a microscope before synthesis. A microfluidic device was fabricated from poly-dimethylsiloxane (PDMS) for the SFL system. PDMS was mixed with a curing agent in a 10:1 ratio and degassed under vacuum for 30 min. Degassed PDMS was poured onto an SU-8 master mold.

The microfluidic channel of the SFL system was loaded with the composite monomer solution, aligned on a microscope stage, and subjected to a pressure-driven flow. In every synthesis cycle, the monomer flow was halted (350 ms) and particles were photo-polymerized in the device using UV light filtered through a dichroic filter set (365 nm wavelength light for 100 ns exposure tine). The polymerized particles were then covected into a collection tube for 500 ms. Synthesis occurred at a rate of ~5 particles per second. After synthesis the particles were rinsed. The PUA particles were rinsed 8 times with ethanol: PEG200 (1/1 (v/v)) and stored in ethanol. The PEG particles were rinsed 3 times with 1×TET (1×TE with 0.05% (v/v) Tween 20).

Although PEG-DA and PUA were used for the microparticles in the examples described herein, any di-acrylated monomers that have been used in stop-flow lithography may be used for the encoded region. Further, any di-acrylated monomers into which UCNs (either nanocrystals with modified surfaces or ligands or nanocrystals with unmodified surfaces or ligands) may be well-dispersed can be employed.

Figure 30:
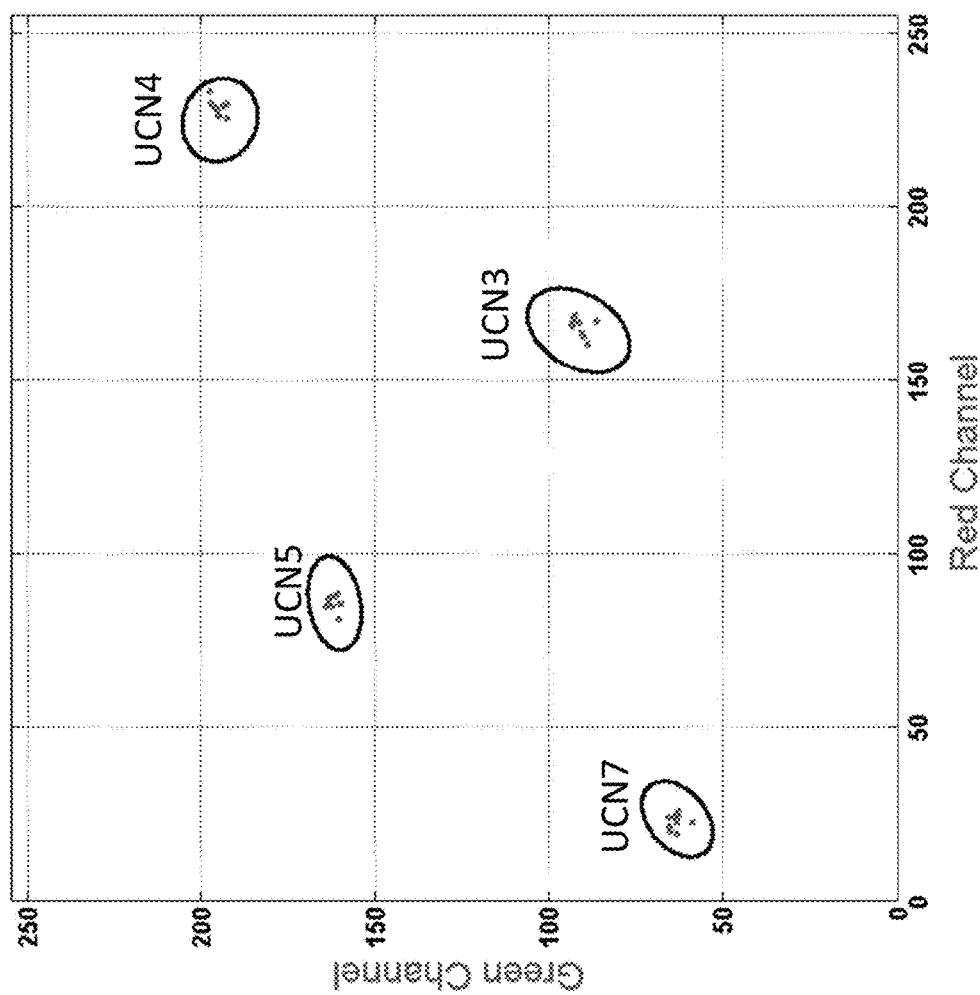
FIG. 30 is a graph of integrated intensity for different color channels for microparticles, in accordance with an embodiment.

In an initial batch of encoded hydrogel microparticles used for testing, each portion of the encoded region included a plurality of nanocrystals selected from the set of types UCN3, UCN4, UCN5 and UCN7, whose characteristics are described above. As used herein, encoded microparticles refers to microparticles that each have one or more portions of the encoded region and that each have one or more types of spectrally distinguishable UCNs. Eight encoded microparticles were illuminated with the NIR diode laser and imaged using a standard CCD image sensor. The integrated intensity was calculated for the red and green channels of the image sensor. FIG. 30 is a plot of the green channel integrated intensity vs. the red channel integrated intensity for each portion of the encoded region in the eight microparticles. As shown, the integrated intensities for the portions of the encoded regions are clumped into groups corresponding to the UCN3, UCN4, UCN5 and UCN7 nanocrystals types. The ellipses are the five-sigma Gaussian fits to the data from the particles having only one type of nanocrystals, which may be considered the "training data." All of the data points for the encoded particles fell within the five-sigma Gaussian fit for the training data.

The encoded microparticles can be used for many different types of labeling application. In some embodiments a representative population of particles covers a large portion of the packaged surface. In some embodiments an individual code consisting of a sequence or grouping of multiple particles placed at a well-defined location. A sequence or grouping of particles on a surface can be used to uniquely identify an object with an encoding capacity of $(C^S)^N$ for asymmetric particles and $(C^S/2)^N$ for symmetric particles, where N is the number of particles deposited. Randomly embedding 10 particles from a set of just 1000 unique asymmetric particles yields an encoding capacity of $\sim(1000)^{10}$, or $10^{30}$, enough to uniquely barcode every manufactured product on Earth.

Figure 31:
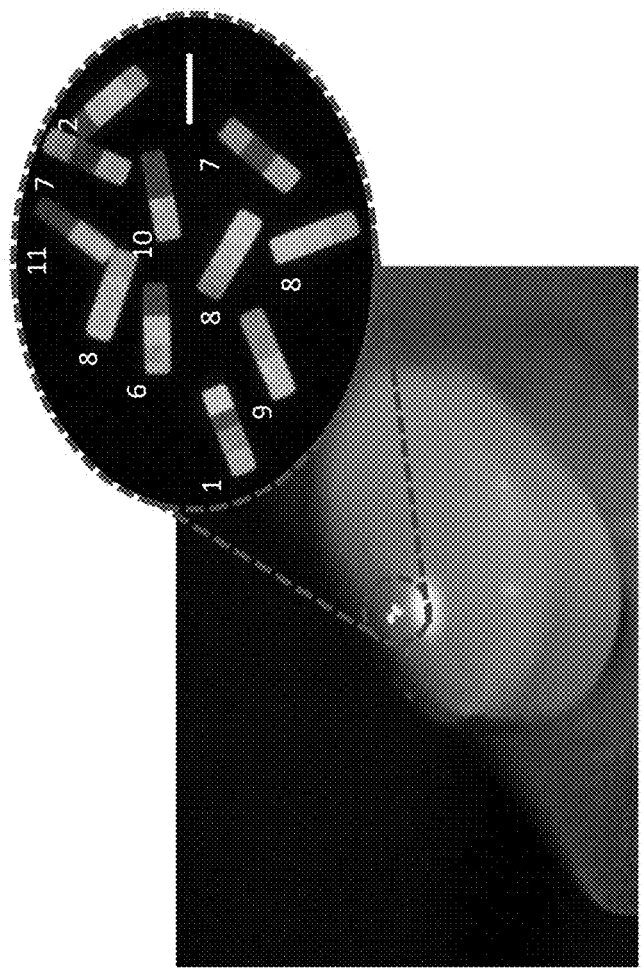
FIG. 31 is a luminescence image of microparticles labeling a blister pack, in accordance with some embodiments.

The inventors used a combination of two portion (two stripe), three portion (three stripe) and, four portion (four stripe) encoded microparticles with each stripe including one of the UCN1-UCN9 types of nanoparticles for labeling a polyvinyl chloride (PVC) blister pack material as shown in FIG. 31. The encoded particles were dispersed in a laminating solution, specifically, 9:1 by volume solution of PUA/photoinitiator. Two microliters of prepolymer solution was dropped onto the blister pack. After ten minutes, the PUA was crosslinked with 365 nm UV light for 30 s.

Figure 32:
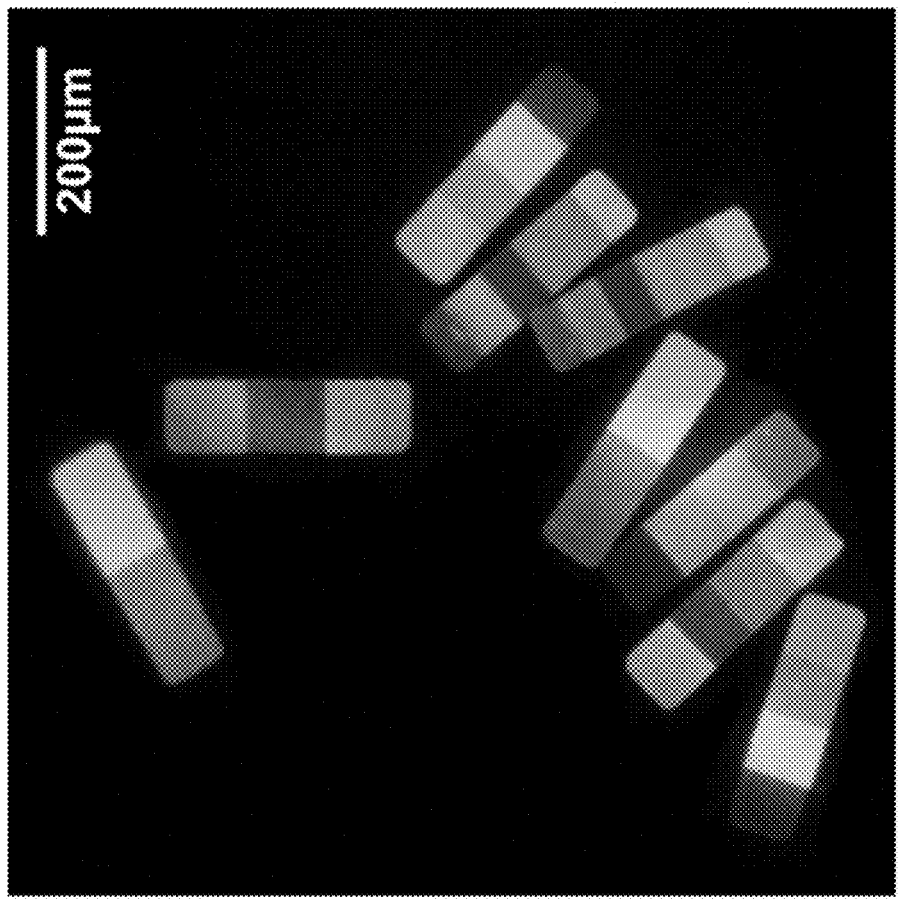
FIG. 32 is a close up of a luminescence image of microparticles labeling a blister pack, in accordance with some embodiment.

FIG. 31 shows the blister pack illuminated with a 1 W 980 nm NIR laser. PUA particles and the surrounding laminate have identical refractive indices, rendering them invisible unless illuminated with the proper NIR source. The detail view of FIG. 31 shows the microparticles imaged using a microscope under 980 nm laser illumination. In the image, the overall color of each portion is readily distinguishable. FIG. 32 is another luminescence image of encoded PUA particles laminated on a pharmaceutical blister pack. In FIG. 32, each of the microparticles has between 2 to 6 coding portions.

Figure 33:
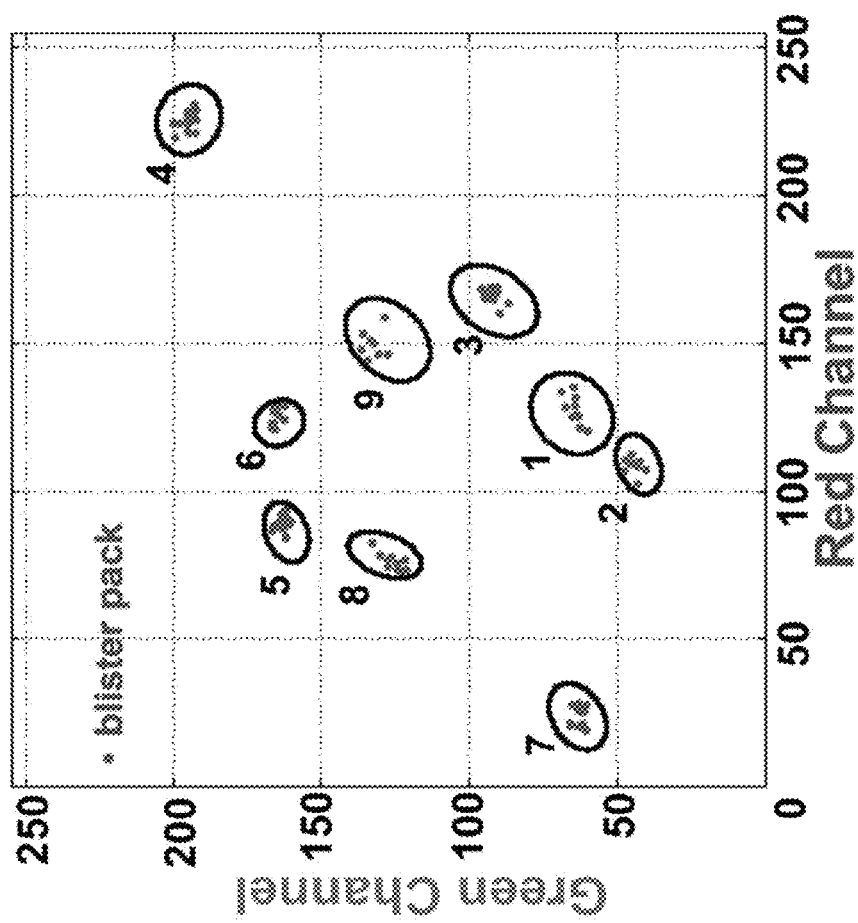
FIG. 33 is a graph of integrated intensity data for portions or stripes of the encoded microparticles on the blister pack, in accordance with an embodiment.

Further, FIG. 33 includes a graph of the integrated intensity of each portion of each microparticle for the red and green color channels. The tight clustering establishes that the spectral signatures of each portion or stripe are readily distinguishable. Further, all of the data falls within the five sigma uncertainty limit determined from the training set of single color hydrogel microparticles. Despite the complex background of the blister pack surface, all decoded spectra fell within 5 sigma of the training centroids. Remarkably, PUA-based RGB training data is not required, as shown by successful use of PEGDA-based training data for UCNs 3-5 and 7 (FIG. 33).

Figure 34:
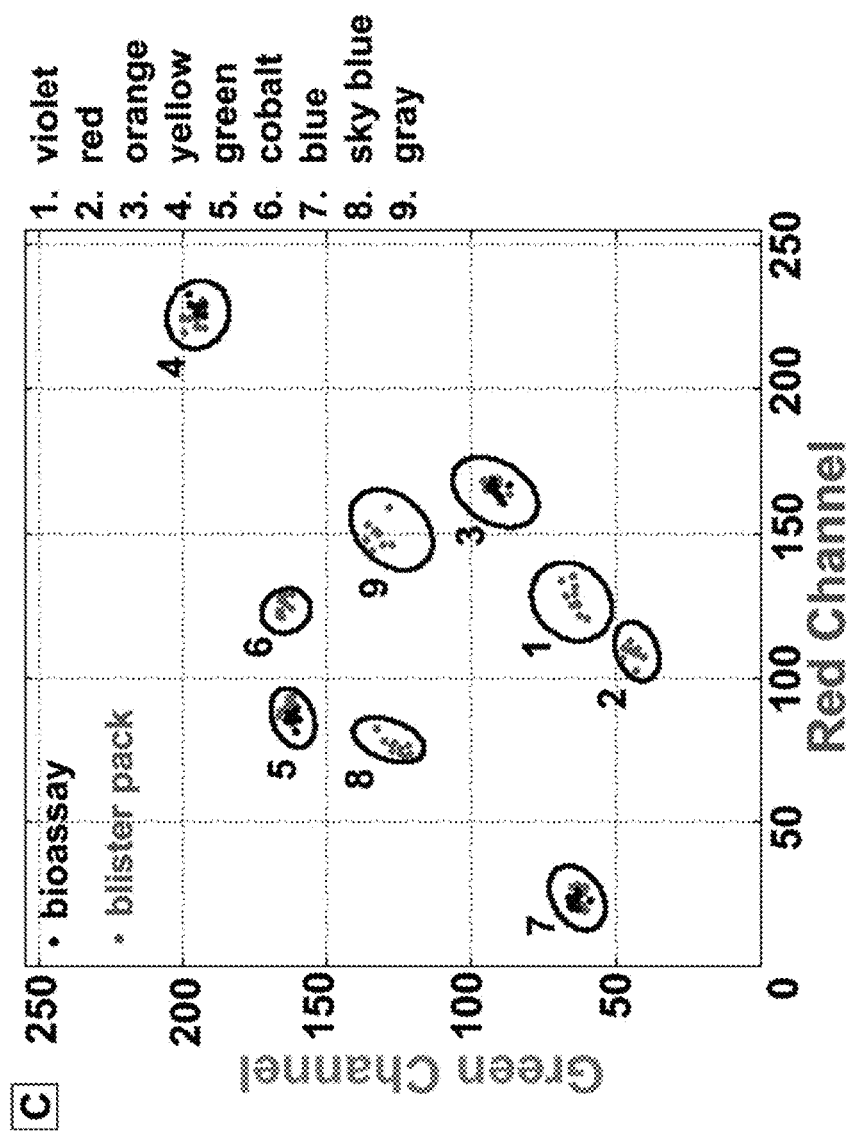
FIG. 34 is a graph of integrated intensity data in red and green channels for portions or stripes of encoded PUA microparticles and encoded PEG microparticles, in accordance with some embodiments.

FIG. 34 is a graph of integrated intensity of each portion of each microparticle for the red and green color channels for both PEG-DA microparticles used for a bioassay and PUA microparticles used for labeling of a blister pack. As shown, the data fits within the five-sigma contours for both types of microparticles, establishing that the reliability of identification applies across different microparticle materials.

Figures 35, 36:
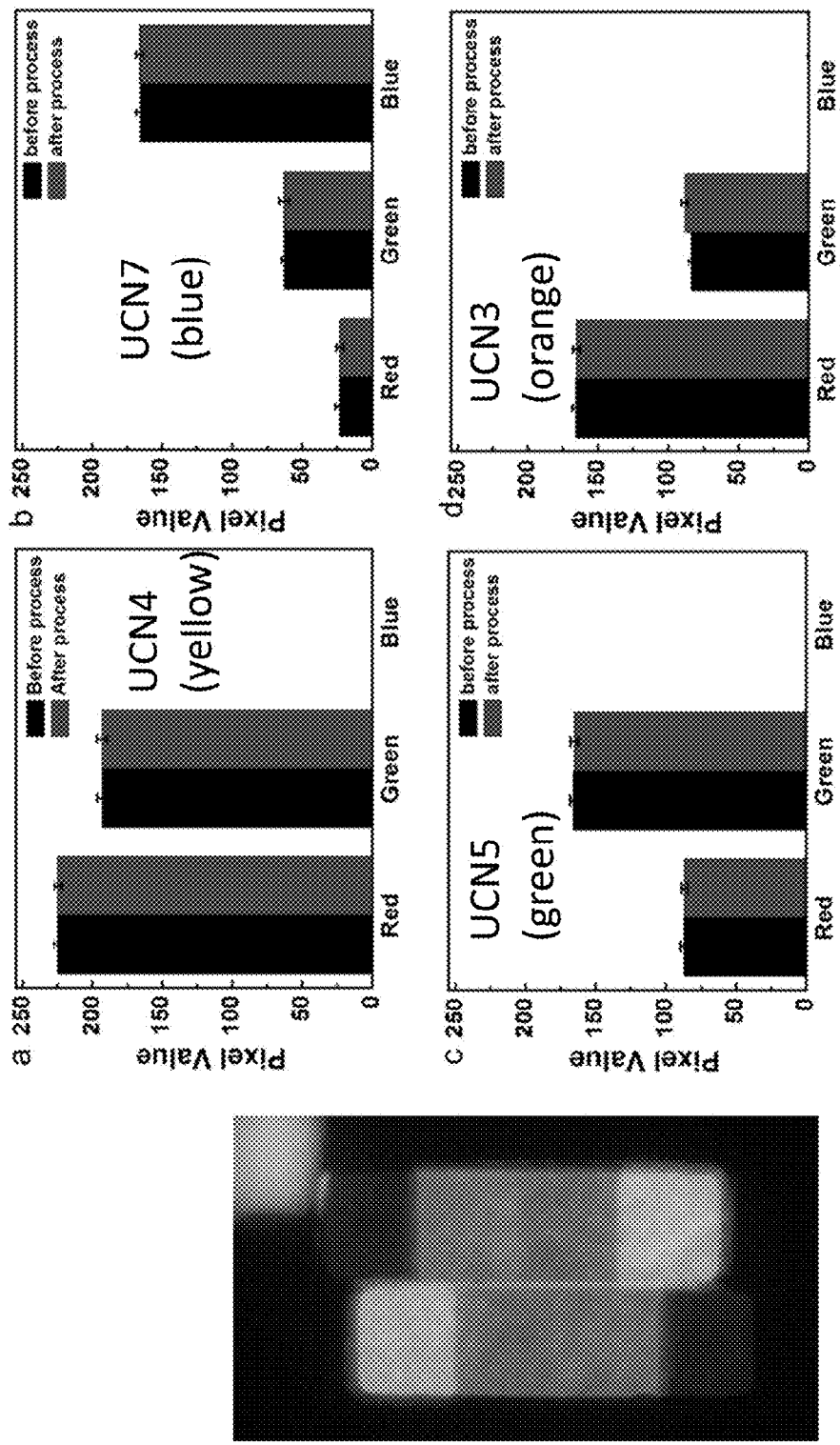
FIG. 35 is a luminescence image of encoded microparticles after simulated PET processing, in accordance with an embodiment.
FIG. 36 includes graphs of integrated intensity for the encoded microparticles before and after simulated PET processing, in accordance with an embodiment.

The PUA microparticles withstand exposure to high-temperature casting up to 260° C. in molten plastics as ubiquitous as poly(ethylene terephthalate) (PET) with no impact on decoding, unlocking applications where durable, embedded barcodes are of use. The inventors experimentally established that the PUA microparticles can withstand conventional polyethylene terephthalate (PET) processing. To simulate PET processing, the PUA encoded microparticles were loaded into a vial containing PET granules. The vial containing the mixture of PUA microparticles and PET chips was heated to 260° C. until the PET granules completely melted. The melted microparticle and PET solution was dropped onto a bottom glass slide and then sandwiched by a top glass slide. The sandwiched glass slides were reheated until the sandwiched solution was dispersed to produce an even PET film. Luminescence images were obtained before and after the melting process. FIG. 35 is a luminescence image of two PUA encoded microparticles illuminated with NIR light after simulated PET processing. FIG. 36 includes graphs of the integrated intensity for various color codes in 10 microparticles after PET processing. As shown by the graphs in FIG. 36, the emission of the coded microparticles did not appear to be affected by the simulated PET processing, meaning that PUA microparticles could be used in PET source material that undergoes PET processing.

The PUA microparticles are also insensitive to repetitive illumination and ambient light, a distinct advantage over fluorescently labeled particles which must be stored in the dark.

A survey of remaining technical risks might lead one to suspect a need for dense particle packing and an accompanying accuracy tradeoff due to potential particle overlap. However, the small number of particles required eliminates this challenge. For instance, for the deposition of 10 particles with dimensions of ~250×70 microns and a field of view of roughly 10 mm, inter-particle spacing of 300-500 microns at maximum would be needed to provide a comfortable buffer at the edges of the field. In comparison, low-end consumer inkjet printers can reliably space individual dots of ink at 300 dots-per-inch, or one dot every 80 microns, enabling rendering accurate particle deposition.

Figure 38:
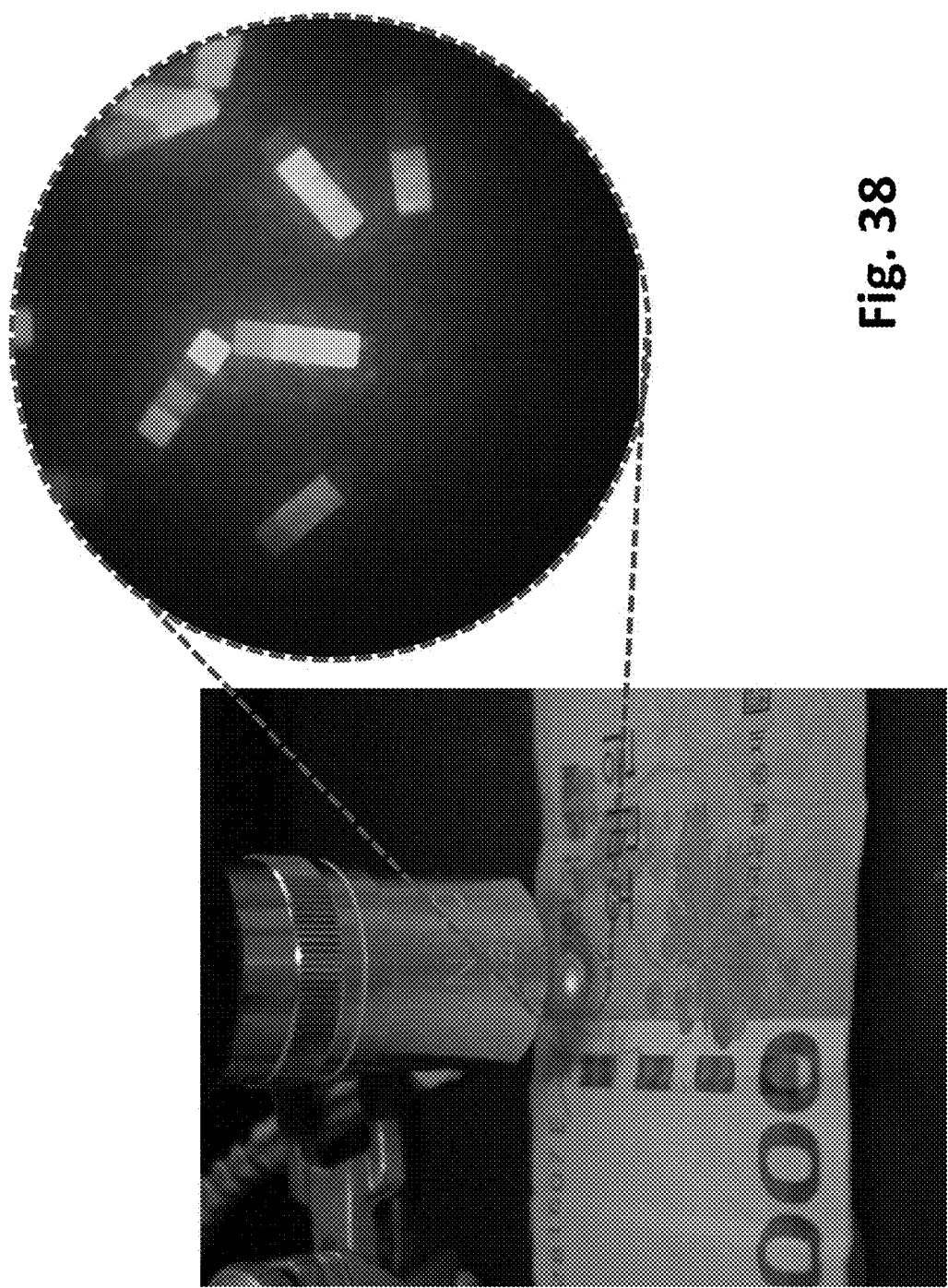
FIG. 38 shows images of microparticles labeling currency, in accordance with an embodiment.

The PUA microparticles can be used for surface labeling of many different types of articles. For example, the inventors coated a polyester thread with microparticles. The particles were mixed in a 9:1 PUA to PI solution, which was used to coat the thread. The solution was then photopolymerized using a 365 nm UV lamp. FIG. 37 includes images of the microparticles coated on the thread under normal illumination in the top image and under NIR illumination in the bottom images. The images under normal illumination show that the microparticles are unobtrusive. The microparticles were also applied to currency as shown in FIG. 38.

Microparticles may be particularly well suited to labeling for anti-counterfeiting purposes because the microparticles are relatively easy to image and it is relatively easy to get quantitative spectral information from the image, but it would be difficult for a counterfeiter to "spoof" the microparticles with spatial/spectral signatures and arrangement of microparticles having the same properties.

The inventors also used the microparticles for labeling of the bulk of objects. For example, FIG. 39 shows a polyvinyl alcohol (PVA) key formed with 3-D printing. The bulk of the PVA key includes about 12 microparticles. As shown in the detail on the left, the microparticles are not visible under normal illumination. However, under NIR illumination, the microparticles can clearly be distinguished.

FIG. 40 shows an acrylonitrile butadiene styrene (ABS) key formed with 3-D printing that includes about 12 microparticles in the bulk of the key. As shown in the detailed view on the left, under normal illumination the microparticles are not visible. However, the microparticle can clearly be distinguished under NIR illumination. The inventors also embedded microparticles in the bulk of a polylactic acid (PLA) key.

In the PVA, ABS and PLA keys, the microparticles were embedded in the bulk of the key by coating them on plastic filaments that were passed through the extruding element of the 3D printer. However, in other embodiments, the microparticles could be added to the bulk of a material before forming or molding the material (e.g., via injection molding or blow molding).

Figure 41:
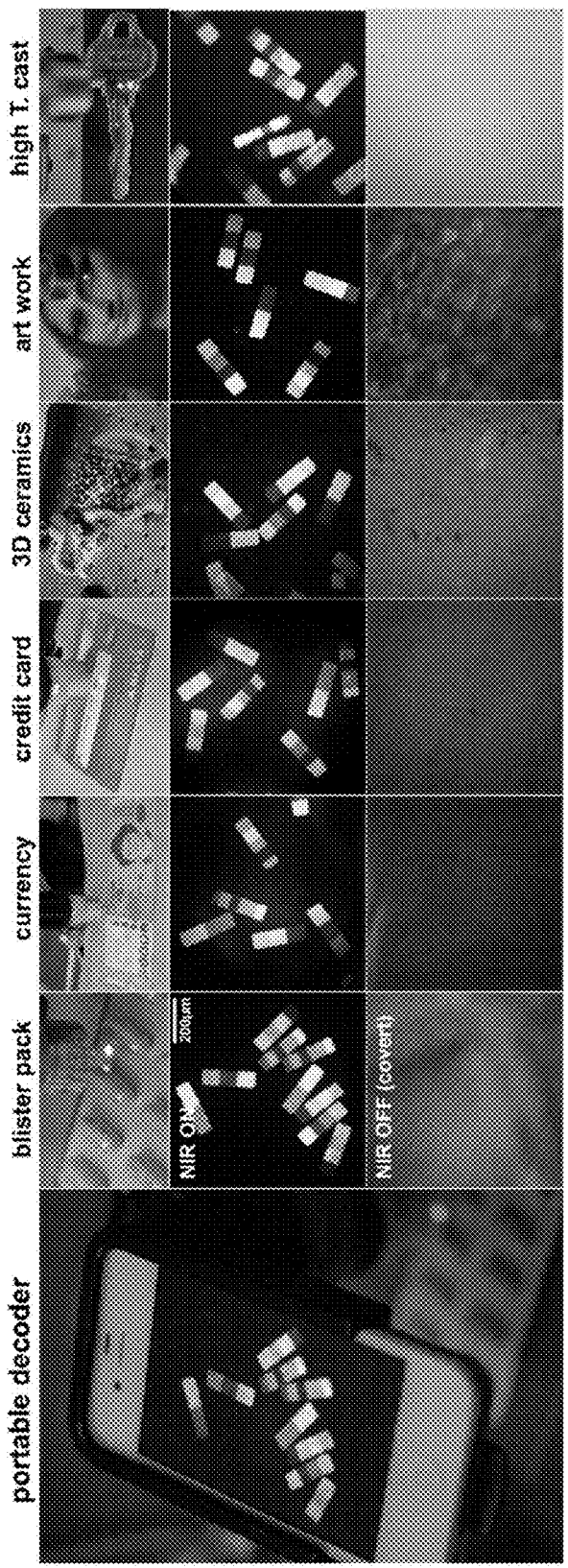
FIG. 41 includes images of microparticles used for labeling a blister pack, currency, a credit card, 3D ceramic, art work and a high temperature cast object, in accordance with an embodiment.

For example, a polystyrene key was cast at high temperature with microparticles in the bulk of the material (see FIG. 41). Silicone molding material was poured onto a key and cured for 24 hours to generate a mold. UCN-integrated PUA particles in a solution of PUA/PI at a ratio of 9:1 (v/v) were dropped into the mold and cured for 30 s using a 365 nm hand-held UV lamp. The key-shaped mold was filled with polystyrene (MW=280,000) granules and heated at 260° C. for 90 min. The silicone mold was cooled to room temperature and the cast object was taken off the mold. Luminescence images were then taken using customized portable decoder under excitation from a 1 W 980 nm NIR laser.

In applications where it is important that the microparticles cannot be seen under ordinary illumination with visible light, the polymer material for the microparticle may be selected to match the refractive index of the material to which the microparticle will be attached. For surface labeling applications, the polymer material of the microparticle may be selected to match the refractive index of a coating material used to attach the microparticles to the underlying object. For labeling within the body of an object, the polymer material of the microparticle may be selected to match a refractive index of the body of the object.

In some embodiments, various types of microparticles could be used as embedded labels for tissues.

As illustrated by the images of FIG. 41, microparticles can be used for labeling the surface and/or the bulk of various types of objects. The microparticles are unobtrusive or "covert" under normal illumination, but clearly visible under NIR illumination. Notably, decoding is not limited to microscope-based instrumentation. FIG. 41 illustrates a image acquisition for a portable decoder that employs a portable apparatus consisting of a mobile phone camera fitted with an objective. Specifically, a portable microscope decoder was assembled using the following components: a mobile phone with a build in camera, a DIN Objective to 10× Eyepiece Tube Assembly, a 20× Objective (long working distance (LWD) Magnification 20×/Numerical aperture (0.30)), and a mobile phone adapter to a microscope eyepiece. FIG. 41 includes images of microparticles used for labeling a pharmaceutical blister pack, currency, a credit card, 3D ceramic objects, art work and a high temperature cast polystyrene key.

Figure 42:
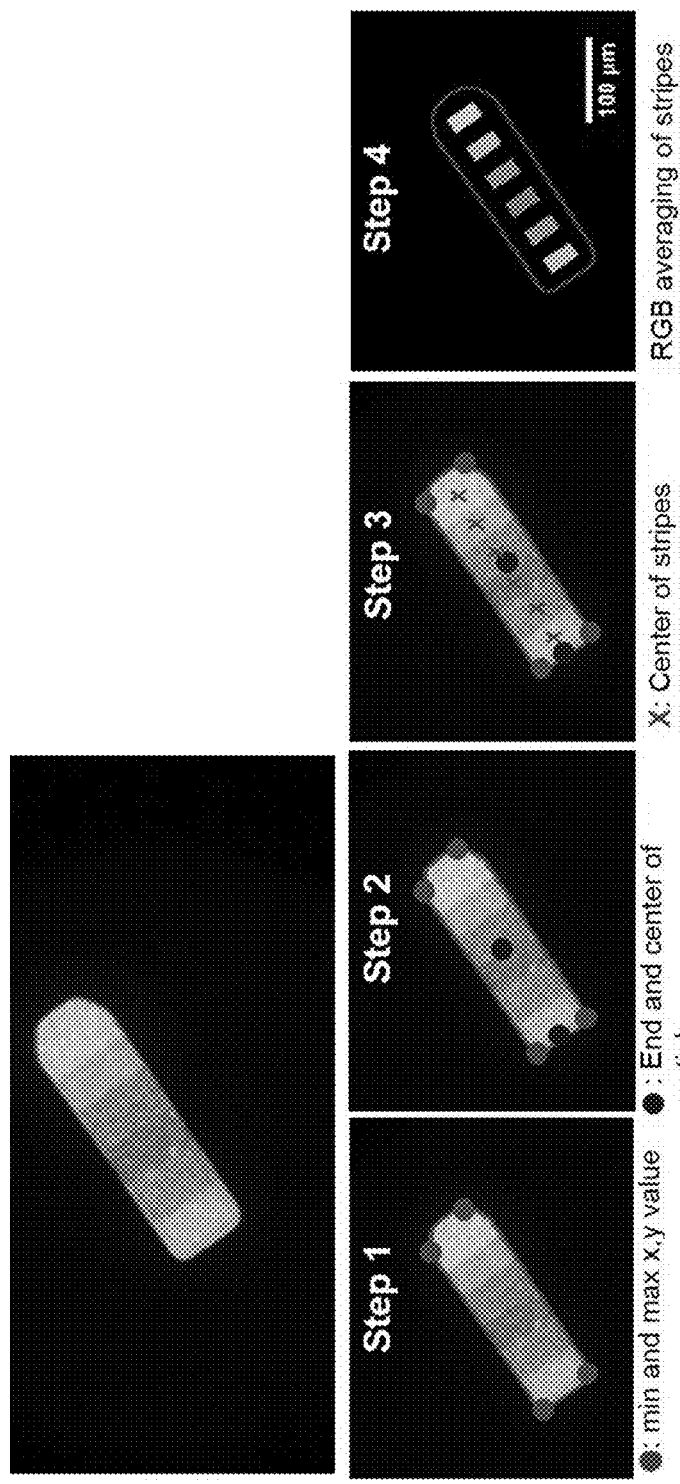
FIG. 42 includes images of a process of reading out spectral codes from a luminescence image of a microparticle, in accordance with some embodiments.

FIG. 42 illustrates a method of reading out the spectral codes of a microparticle in accordance with some embodiments of the invention. Initially, a maximum or minimum is identified along the x or y axis (step 1). A center and end points of the particle are identified (step 2). A particle orientation is determined and, in the case of an asymmetric particle, a direction of the particle is determined, and the center of each stripe is identified (step 3). An average RGB value is calculated within a sampled area around each stripe (step 4).

Specifically, images of particles with 6 stripes were taken via a CCD decoder and loaded into image processing and analysis software (e.g., MATLAB by Mathworks of Natick, Mass.). Particle boundaries were defined using a grayscale intensity-based edge detection algorithm. Boundary pixel x and y values were averaged to determine the particle centroid. Boundary pixels with minimum and maximum x and y values (four points total) were noted, and distances between adjacent points used to determine the particle end point, or the pixel located on the 2nd shortest edge of the particle boundary and its longitudinal axis. The end pixel and centroid pixel were then used to determine both the code orientation and a director for the particle's longitudinal axis. The centroid of each striped region of the particle was determined by segmenting the particle into six regions (the number of stripes were presumed known a priori) along its longitudinal director. In other embodiments, k-means image segmentation algorithms may be employed to define regions of the particle based on color, without a priori knowledge of the number of particle stripes. RGB values were measured by averaging pixels within each of the six striped regions of particles under test were compared against training RGB values and standard deviations, as determined from a particle training set. If an average set of RGB values fell within 3.5 standard deviations of a training RGB value, the values were determined to match. In this way, 'analog' RGB sequences were translated into 'digital' sequences of spectral signatures.

Figure 43:
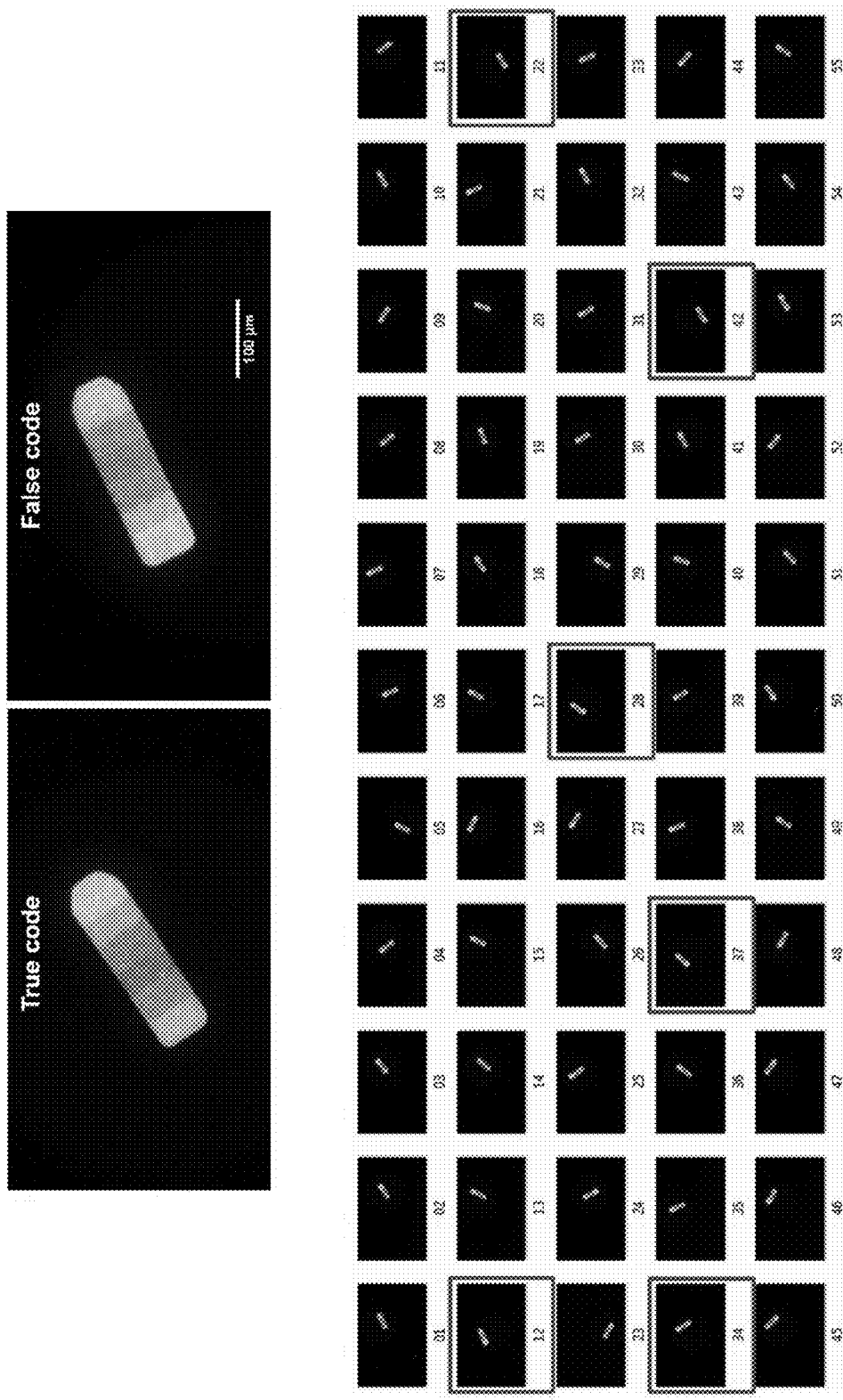
FIG. 43 includes images used to distinguish two different codes of microparticles, in accordance with an embodiment.

To test the identification, multiple microparticles were generated with a "true code" and some with a different "false code" as shown in FIG. 43. An automated decoding system employing the process described above with respect to FIG. 42 correctly distinguished the "true code" microparticles that matched a provided "authentic code" from the "false code" microparticles that did not match the provided authentic code, using luminescence images. In FIG. 43, the identified "false code" images are indicated with a box around the image.

Further details regarding an exemplary system of particle synthesis are provided below. FIG. 44 schematically depicts a flow lithography and decoding system for particle synthesis that includes a flow lithography microscope setup, a decoding microscope setup, and a spectrometer setup. FIG. 45 is an image flow lithography and decoding system for particle synthesis. The flow lithography microscope setup includes a UV LED light source, a 10× objective (Edmund optics), a CMOS camera, a dichroic cage cube, a dichroic mirror, cage cube-mounted turning prism mirrors, an XYZ sample stage, a mask holder, Ø1" lens tubes, an XY translator, a high-precision zoom housing for Ø1" optics, a 30 mm cage, posts, an LED and valve control relay, which were controlled with instrument control hardware and software, a camera adapter, and a CCD camera. The decoding microscope setup included a 1 W 980 nm laser, a 950 nm cut-on filter, a collimator, a CCD camera adapter, and a CCD camera. The spectrometer setup included a spectrometer, a laser translation stage, an X, Y translating lens mount, NIR achromatic doublet pairs, a collimator, a 950 nm cut-on filter, a 30 mm cage, and posts.

The versatile, high-performance stop-flow lithography (SFL) systems and techniques described herein are a high throughput process for synthesizing particles. In a semicontinuous process, multiple coflowing laminar streams—each containing a single optically active UCN moiety or probe molecule—are convected into a microchannel (e.g., formed from poly(dimethylsiloxane) (PDMS) or a non-swelling thiolene-based resin for use with organic solvents), stopped, and photopolymerized in place via mask-patterned ultraviolet light (365 nm) to form barcoded particles at a rate of 18,000 particles/hr, which are then displaced when flow resumes. This $\sim 10^4$ particles/hr synthesis rate is by no means limiting; hydrodynamic flow focusing has been used to increase the synthesis rate for similar particles to over $10^5$ particles/hr. The synthesis platform may also be constructed using commercial off-the-shelf parts and free-standing optics. Parallelization in an industrial setting, with no further optimization, could readily increase the facility-scale synthesis throughput by orders of magnitude to meet industrial demand.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention. Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

What is claimed is:

1. A label for an article, the label comprising:
a plurality of microparticles each having a body formed from a polymer material, each microparticle including an encoded region having a plurality of portions, the plurality of portions for a first microparticle in the plurality of microparticles including:
a first plurality of spectral encoding elements having a first spectral signature disposed in a first portion of the encoded region; and
a second plurality of spectral encoding elements having a second spectral signature disposed in a second portion of the encoded region spatially separated from the first portion of the encoded region enabling spatial encoding of the first microparticle, the second spectral signature being different from the first spectral signature enabling spectral encoding of the first microparticle.

2. The label of claim 1, wherein the encoded region of each microparticle includes between two and six portions.

3. The label of claim 1, wherein at least one particle in the plurality of microparticles is magnetic.

4. The label of claim 1, wherein the plurality of microparticles includes between 2 and 10 microparticles.

5. The label of claim 1, wherein a shape of the first microparticle is different than a shape of a second microparticle in the plurality of microparticles.

6. The label of claim 1, wherein a shape of the first microparticle comprises at least one of an asymmetric shape, a circular shape, a triangular shape, a pentagonal shape, a square shape, or a non-rectangular shape.

7. The label of claim 1, wherein the first microparticle further comprises a probe region including a molecular recognition element.

8. The label of claim 7, wherein the molecular recognition element comprises a nucleic acid, microRNA (miRNA), single-stranded (ssDNA), a protein, a receptor protein, an antibody, an enzyme, a peptide, an aptamer, an avimer, an Fc domain fragment, a phage, a carbon nanotube sensor, or a peptide.

9. The label of claim 7, wherein the probe region at least partially overlaps one or more of the plurality of portions of the encoded region.

10. The label of claim 1, wherein the encoded region of the first microparticle has a first spatial-spectral pattern of portions with associated spectral signatures; and
wherein the plurality of microparticles includes a second microparticle including an encoded region having a second spatial-spectral pattern of portions with associated spectral signatures, wherein the first spatial-spectral pattern is different than the second spatial-spectral pattern.

11. The label of claim 1, wherein the plurality of microparticles is disposed on a surface of the article.

12. The label of claim 1, wherein at least some of the plurality of microparticles are disposed in a bulk of the article.

13. The label of claim 1, wherein coded information is provided by the spatial and spectral signature of each microparticle and by one or more of orientation, shape, and arrangement of the microparticles.

14. The label of claim 1, wherein the label is an anti-counterfeiting label.

15. The label of claim 1, wherein a refractive index of a material of the body of the microparticles matches a refractive index of a material of the article to be labeled under normal illumination with visible light such that, when the article is labeled with the coded label, the microparticles are not visible under normal illumination with visible light.

16. The label of claim 1, wherein the article comprises plastic and the plurality of microparticles are disposed in a bulk of the article.

17. The label of claim 1, wherein the article comprises one or more of: a fiber, currency, a credit card, a plastic object, or a work of art.

18. The label of claim 1, wherein the plurality of microparticles is disposed in or on packaging for an article.

19. The label of claim 1, wherein the distance between microparticles is in a range from 300 to 500 micrometers.

20. The label of claim 1, wherein the plurality of portions for the first microparticle in the plurality of microparticles further includes a third plurality of spectral encoding elements having a third spectral signature disposed in a third portion of the encoded region spatially separated from the first portion of the encoded region and spatially separated from the second portion of the encoded region, the third spectral signature being different from the first spectral signature and the second spectral signature.

21. The label of claim 1, wherein the first portion of the encoded region forms a first stripe of the microparticle and the second portion of the encoding region forms a second stripe of the microparticle.

* * * * *